(12) United States Patent
Jacobi

(10) Patent No.: US 8,067,583 B2
(45) Date of Patent: Nov. 29, 2011

(54) METHOD FOR SYNTHESIZING FURANOSTEROIDS

(75) Inventor: Peter A. Jacobi, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 537 days.

(21) Appl. No.: 11/949,991

(22) Filed: Dec. 4, 2007

(65) Prior Publication Data

US 2009/0143346 A1 Jun. 4, 2009

Related U.S. Application Data

(60) Provisional application No. 60/871,884, filed on Dec. 26, 2006.

(51) Int. Cl.
*C07J 71/00* (2006.01)
(52) U.S. Cl. .......................................... 540/93
(58) Field of Classification Search ............ 540/93
See application file for complete search history.

(56) References Cited

OTHER PUBLICATIONS

Anderson et al., "Synthesis of the Furanosteriodal Antibiotic Viridin", Agnew Chem Int Ed 2004 43:1998.
Boynton et al. "The Preparation of Furano-steroid Analogues of Demethoxyviridin", J Chem Research 1999 638-639.
Broka et al., "Synthetic Studeis on Wortmannin and 11-Desacetoxywortmannin", J. Org. Chem 1992 57:4888-4894.
Burgueno-Tapia et al., "Cacalolides from *Senecio madagascarienis*", J. Nat. Prod. 2001 64:518-521.
Carlini et al., "Intramolecular Diels-Alder and Cope Reactions of o-Quinonoid Monoketals and Their Adducts:Efficient Syntheses of (+)-Xestoquinone and Heterocycles Related to Viridin", J. Org. Chem. 1997 62:2330-2331.
Freiermuth et al., "Tautomerization of Phenols—The Anthrone-Anthrol Equilibrium in Aqueous Solution", Helvetica Chimca Acta 2001 84:3796-3809.
Garduno-Ramirez et al., "New Modified Eremophilanes from the Roots of *Psacalium radulifolium*", J. Nat. Prod. 2001 64:432-435.
Honzawa et al., "Synthetic Studies on (+)-Wortmannin. An Asymmetric Construction of an Allylic Quaternary Carbon Center by a Heck Reaction", Tetrahedron Letters 1999 40:311-314.
Kelly et al., "Synthesis of (+)-Fredericamycin A", J. Am. Chem. Soc. 1988 110:6471-6480.
Mizutani et al., "Total Synthesis of (+)-Wortmannin", Agnew. Chem. Int. Ed. 2002 41(24):4680-4682.
Moffat, J.S., "Biridin. Part IV. Total Synthesis of a Tetracyclic G16 Degradation Product", J. Chem. Soc. 1966 734-743.
Sato et al., "The First Chemical Synthesis of Wortmannin by Starting from Hydrocortisone", Tetrahedron Letters 1996 37(34):6141-6144.
Souza et al., "Progress towards viridin:synthesis of the pentacyclic furanosteroid ring system via o-benzoquinonoid cycloadditions", Chem. Commun. 1999 1947-1948.
Torres et al., "Furanoeremophilanes from *Senecio linifolius*", Phytochemistry 1989 28(11):3093-3095.
Van De Water et al., "New Construction of Ortho Ring-Alkylated Phenols via Generation and Reaction of Assorted o-Quinone Methides", J. Am. Chem. Soc. 2000 122:6502-6503.
Wipf et al., "Chemistry and biology of wortmannin", Org. Biomol. Chem. 2005 3:2053-2061.
Wright et al., "Studies on the sequential multi-component coupling/Diels-Alder cycloadditin reaction", Tetrahedron Letters 2002 43:943-946.

*Primary Examiner* — Barbara P Badio
(74) *Attorney, Agent, or Firm* — Licata & Tyrrell P.C.

(57) ABSTRACT

The present invention is a method for synthesizing furanosteroids. The method involves intramolecular Diels-Alder/retro-Diels-Alder reaction and tautomerization of a functionalized alkyne oxazole to produce a furo[2,3-b]phenol derivative which is elaborated by intermolecular and intramolecular condensations to generate ring-A of the furanosteroid. Furanosteroids and pharmaceutical compositions containing the same are also provided.

1 Claim, No Drawings

METHOD FOR SYNTHESIZING FURANOSTEROIDS

This application claims benefit to U.S. Provisional Application No. 60/871,884 filed Dec. 26, 2006.

BACKGROUND OF THE INVENTION

The furanosteroids are a class of novel pentacyclic fungal metabolites that share in common a furan ring bridging positions 4 and 6 of the steroid skeleton (MacMillan, et al. (1968) *Chem. Commun.* pg. 613; MacMillan, et al. (1972) *J. Chem. Soc., Chem. Commun.* pg. 1063; MacMillan, et al. (1972) *J. Chem. Soc. Perkin I* pg. 2892; MacMillan, et al. (1972) *J. Chem. Soc. Perkin I* pg. 2898; Simpson, et al. (1978) *J. Chem. Soc. Perkin I* pg. 979; Haefliger, et al. (1973) *Helv. Chim. Acta* 56:2901; Brian & McGowan (1945) *Nature* (London) 156:144; Aldridge, et al. (1975) *J. Chem. Soc. Perkin I* pg. 943; Hanson, et al. (1985) *J. Chem. Soc. Perkin Trans I* pg. 1311; Hanson (1995) *Nat. Prod. Rep.* pg. 381; Wipf & Kerekes (2003) *J. Nat. Prod* 66:716-718).

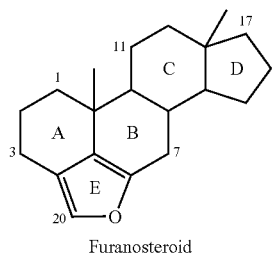

Furanosteroid

Members of this class are known for their powerful anti-inflammatory and antibiotic properties (Brian & McGowan (1945) supra). These compounds have also been shown to selectively block certain intracellular signaling pathways, in particular those associated with cell growth and development (Powis, et al. (1994) *Cancer Res.* 54:2419; Ward, et al. (2003) *Chem. Biol.* 10:207; Liu, et al. (2005) *Chem. Biol.* 12:99-107). As such, furanosteroids are useful as therapeutic agents for diseases characterized by rapid cell proliferation, including cancer (Ward, et al. (2003) supra). Representative examples include members of the viridin and wortmannin families, distinguished by an aromatic ring C in the former and a strained lactone ring A in the latter. The growth inhibitory properties of these compounds stem partly from their activity as irreversible inhibitors of phosphoinositide 3-kinase (PI3K), a class of enzymes that play a key role in important cell signaling processes (Powis, et al. (1994) supra). In addition, wortmannin has been shown to inhibit mammalian Polo-like kinase, a vital enzyme in cellular growth cycles.

Structure-activity studies have identified C20 of the furanosteroid skeleton in both families as a crucial site for PI3-kinase inhibition, most likely due to the highly electrophilic nature of the furan ring (Norman, et al. (1996) *J. Med. Chem.* 39:1106; Wymann, et al. (1996) *Mol. Cell. Biol.* 16:1722; Dodge, et al. (1995) *Biorg. Med. Chem. Lett.* 5:1713; Haefliger, et al. (1975) *Helv. Chim. Acta* 58:1620; Haefliger & Hauser (1975) *Helv. Chim. Acta* 58:1629; Walker, et al. (2000) *Mol. Cell.* 6:909; Wipf, et al. (2004) *Org. Biomol. Chem.* 2:1911-1920). It is believed that irreversible inhibition occurs by nucleophilic addition of the kinase to C20, a process that is facilitated by the C3 and C7-carbonyl groups. In vitro studies support this, since both amines and thiols rapidly open the furan ring (Wymann, et al. (1996) supra). This reactivity has been exploited to prepare a library of ring-opened analogs of wortmannin, some of which have superior activity/selectivity profiles compared to the parent compound (Wipf, et al. (2004) supra). Also, modifications in ring D have shown this region to be an important enzyme recognition site. For example, 17β-OH wortmannin, with an $IC_{50}$ of 0.5 nM, was the first known subnanomolar inhibitor of PI3-kinase, indicating that even more potent members of this class might be developed (Dodge, et al. (1995) supra).

However, analysis of wortmannin and viridin derivatives has been hindered by the many difficulties associated with synthesizing these compounds (Broka & Ruhland (1992) *J. Org. Chem.* 57:4888; Sato, et al. (1996) *Tetrahedron Lett.* 37:6141; Honzawa, et al. (1999) *Tetrahedron Lett.* 40:311; Mizutani, et al. (2002) *Angew. Chem. Int. Ed.* 41:4680; Wipf & Kerekes (2003) 225th ACS National Meeting, New Orleans, La.; Wipf & Halter (2005) *Org. Biomol. Chem.* 3:2053-2061; Moffatt (1966) *J. Chem. Soc.* (C) pg. 734; Yasuchika, et al. (1987) *Chem. Commun.* pg. 515; Carlina, et al. (1997) *J. Org. Chem.* 62:2330; Souza & Rodrigo (1999) *Chem. Commun.* pg. 1947; Boynton, et al. (1999) *J. Chem. Research* (S) pg. 638; Wright, et al. (2001) 221st ACS National Meeting; Wright, et al. (2002) *Tetrahedron Lett.* 43:943; Anderson, et al. (2004) *Angew. Chem. Int. Ed.* 43:1998). Only one total synthesis of viridin has been reported (Anderson, et al. (2004) supra), and two syntheses of wortmannin (Sato, et al. (1996) *Tetrahedron Lett.* 37:6141; Mizutani, et al. (2002) *Angew. Chem. Int. Ed.* 41:4680). The furanosteroid skeleton itself has also proven to be a significant synthetic challenge. Therefore, to synthesize structural analogs of known furanosteroids, there is a need in the art for a concise synthetic approach for preparing the furanosteroid skeleton. The present invention meets this need in the art.

SUMMARY OF THE INVENTION

The present invention is a method for synthesizing a furanosteroid. The method involves transforming a functionalized alkyne oxazole to a furo[2,3-b]phenol derivative by an intramolecular Diels-Alder/retro-Diels-Alder reaction and tautomerization; and elaborating the furo[2,3-b]phenol derivative by intermolecular and intramolecular condensations thereby synthesizing a furanosteroid. Furanosteroids and pharmaceutical compositions containing the same are also provided.

DETAILED DESCRIPTION OF THE INVENTION

A novel method for synthesizing a furanosteroid has now been established. The method involves directly transforming a functionalized alkyne oxazole to a furo[2,3-b]phenol derivative by an intramolecular Diels-Alder/retro-Diels-Alder reaction and tautomerization; and elaborating the furo[2,3-b]phenol derivative by intermolecular and intramolecular condensations thereby generating the furanosteroid.

The instant method is presented schematically in Scheme 1, wherein an alkyne oxazole of the structure I is transformed directly to a furo[2,3-b]phenol derivative II by a sequence involving intramolecular Diels-Alder/retro-Diels-Alder reaction followed by tautomerization. The resulting tautomer, functionalized phenol II, subsequently participates in both intermolecular and intramolecular phenol-dienone-aldol condensations, as for example in IV→V and VI→VII, generating the A, B, E-ring skeleton III characteristic of furanosteroids such as viridin and wortmannin.

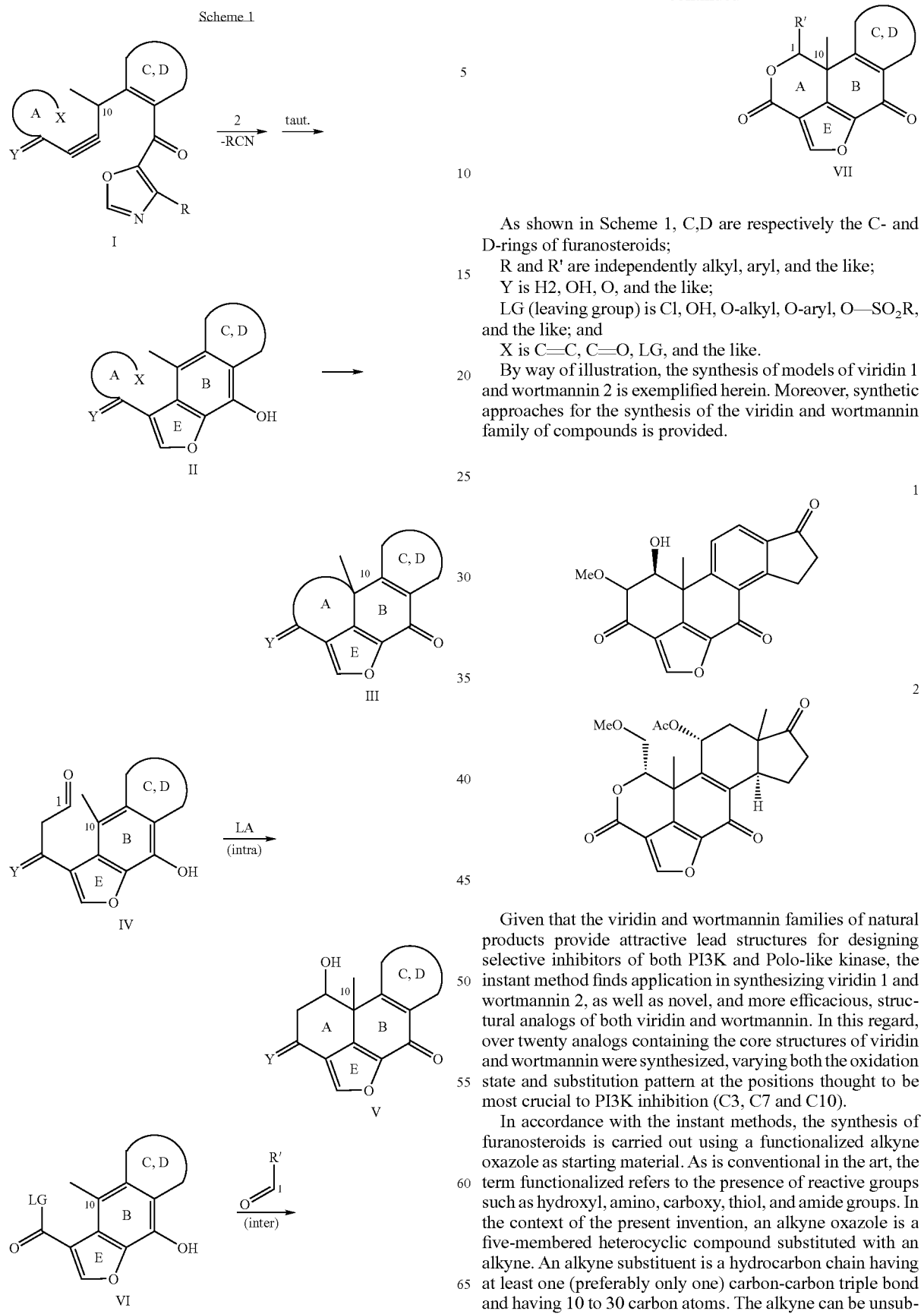

As shown in Scheme 1, C,D are respectively the C- and D-rings of furanosteroids;

R and R' are independently alkyl, aryl, and the like;

Y is H2, OH, O, and the like;

LG (leaving group) is Cl, OH, O-alkyl, O-aryl, O—SO₂R, and the like; and

X is C═C, C═O, LG, and the like.

By way of illustration, the synthesis of models of viridin 1 and wortmannin 2 is exemplified herein. Moreover, synthetic approaches for the synthesis of the viridin and wortmannin family of compounds is provided.

Given that the viridin and wortmannin families of natural products provide attractive lead structures for designing selective inhibitors of both PI3K and Polo-like kinase, the instant method finds application in synthesizing viridin 1 and wortmannin 2, as well as novel, and more efficacious, structural analogs of both viridin and wortmannin. In this regard, over twenty analogs containing the core structures of viridin and wortmannin were synthesized, varying both the oxidation state and substitution pattern at the positions thought to be most crucial to PI3K inhibition (C3, C7 and C10).

In accordance with the instant methods, the synthesis of furanosteroids is carried out using a functionalized alkyne oxazole as starting material. As is conventional in the art, the term functionalized refers to the presence of reactive groups such as hydroxyl, amino, carboxy, thiol, and amide groups. In the context of the present invention, an alkyne oxazole is a five-membered heterocyclic compound substituted with an alkyne. An alkyne substituent is a hydrocarbon chain having at least one (preferably only one) carbon-carbon triple bond and having 10 to 30 carbon atoms. The alkyne can be unsubstituted or substituted with from 1 to 10 substituents, including, but not limited to halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Examples of suitable functionalized alkyne oxazoles of use in accordance with the instant invention are provided, e.g., in Scheme 2.

Intramolecular Diels-Alder/retro-Diels-Alder reactions are routinely carried out by the skilled artisan and any suitable method can be employed in the method disclosed herein.

As used herein, tautomerization refers to the phenomenon wherein a proton of one atom of a molecule shifts to another atom. See, March (1992) *Advanced Organic Chemistry: Reactions, Mechanisms and Structures*, 4<sup>th</sup> Ed., John Wiley & Sons, pages 69-74. The term "tautomer" refers to the compounds produced by the proton shift.

The tautomer resulting from the intramolecular Diels-Alder/retro-Diels-Alder and tautomerization reactions is subsequently involved in intermolecular and intramolecular phenol-dienone-aldol condensations (e.g., nucleophilic displacements, conjugate additions, etc.) to provide the desired furanosteroid. Such reactions are routinely practiced in the art and can be carried out as exemplified herein or under any suitable condition. By way of illustration, both inter- and intramolecular condensations can be achieved using titanium tetrachloride or other Lewis acids (including aluminum chloride, boron trifluoride, $ZnCl_2$, etc). Furanosteroids produced in accordance with the present invention can be used as inhibitors of PI3K and Polo-like kinases in the treatment of a variety of diseases and conditions including cancer, inflammation, and infectious disease. Accordingly, the present invention also relates to pharmaceutical compositions, which contain one or more of the compounds described herein (or a prodrug, pharmaceutically acceptable salt or other pharmaceutically acceptable derivative thereof), in admixture with a pharmaceutically acceptable carrier. In certain embodiments, these compositions optionally further contain one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be a cytotoxic agent or anticancer agent approved for the treatment of cancer. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts or a prodrug or other adduct or derivative of a compound of this invention which upon administration to a patient in need is capable of providing, directly or indirectly, a compound as otherwise described herein, or a metabolite or residue thereof.

As used herein, the term pharmaceutically acceptable salt refers to those salts which are suitable for use in contact with the tissues of humans or other animals without undue toxicity, irritation, allergic response and the like, and are commensurate with a reasonable benefit/risk ratio. Pharmaceutically acceptable salts are well-known in the art. For example, Berge, et al. ((1977) *J. Pharmaceutical Sciences*, 66:1-19) describe pharmaceutically acceptable salts in detail. The salts can be prepared in situ during the final isolation and purification of the compounds of the invention, or separately by reacting the free base function with a suitable organic acid. Examples of pharmaceutically acceptable include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Furthermore, the term pharmaceutically acceptable prodrugs, as used herein, refers to compounds that are rapidly transformed in vivo to yield the parent compound, for example by hydrolysis in blood. The preparation and use of prodrugs is known in the art (see, e.g., Edward B. Roche, ed. (1987) *Bioreversible Carriers in Drug Design*, American Pharmaceutical Association and Pergamon Press).

As described above, the pharmaceutical compositions of the present invention additionally encompass a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington: The Science and Practice of Pharmacy* ((2000) Alfonso R. Gennaro, editor, 20th ed. Lippincott Williams & Wilkins: Philadelphia, Pa.) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethylcellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Novel furanosteroids produced according to the present method can be screened for biological activity using any conventional method. For example, PI3 kinase assays are disclosed by Yuan, et al. ((2005) *Bioconjugate Chem,* 16 (3): 669-675) and Fruman, et al. ((1999) *Science* 283:393-7). Assays for monitoring the assembly of peptide-MHC class II complexes (Song, et al. (1997) *International Immunology* 9:1709-1722) and mast cell exocytosis (Marquardt, et al. (1996) *J. Immunol.* 156:1942-1945) are known in the art as are assays for monitoring cell proliferation.

The invention is described in greater detail by the following non-limiting examples.

Example 1

Synthesis of Alkyne Oxazoles

Using a general procedure for converting salicylaldehyde derivatives to a wide variety of o-substituted phenols (Van De Water, et al. (2000) *J. Am. Chem. Soc.* 122(27):6502), alkyne oxazoles were produced as illustrated in Scheme 2.

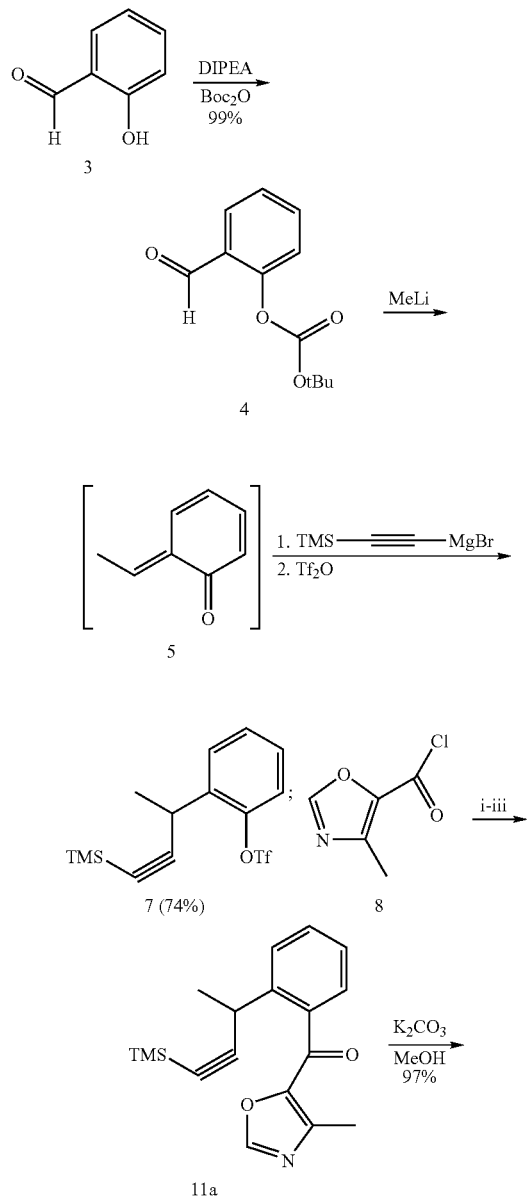

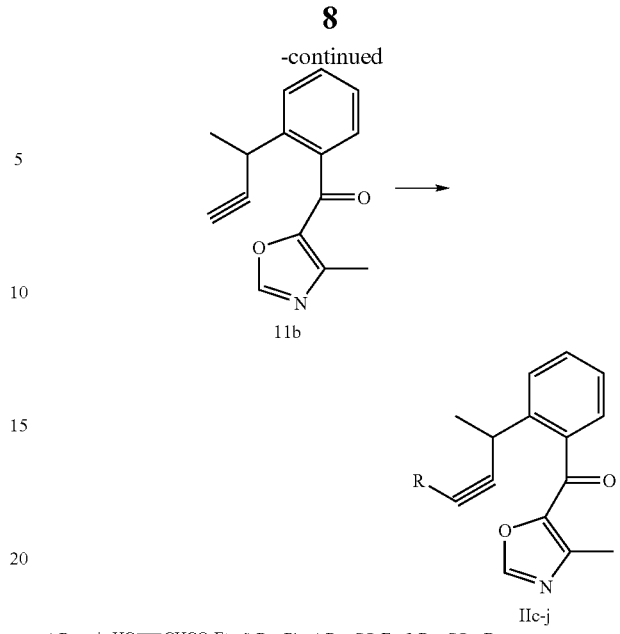

c) R = cis-HC═CHCO$_2$Et, d) R = Ph, e) R = CO$_2$Et, f) R = CO$_2$t-Bu, g) R = CO$_2$Bn, h) R = C(═O)CH$_3$, i) R = I, j) R = CH═O.
i. pinacolborane, Pd(OAc)$_2$, DPEphos, NEt$_3$, 83%. ii. NaIO$_4$, HOAc, 81%. iii. 8, PdCl$_2$(PPh$_3$)$_2$, toluene, K$_3$PO$_4$, 78%.

Parent compound 3 was converted to the Boc-derivative 4. In a very efficient sequence, treatment of 4 with 1.05 eq of MeLi generated the reactive o-quinone methide 5, by a pathway involving nucleophilic addition to the aldehyde, followed by intramolecular transfer of the Boc group and 1,4-elimination. Quenching with the Grignard reagent derived from trimethylsilylacetylene followed by triflation then gave a 74% overall yield of the desired triflate derivative 7 on 95 mmol scales (>20 grams). With gram quantities of 7 in hand, a straightforward, three-step sequence was developed to produce the alkyne oxazole 11a. This three-step process involved (i, ii) elaboration to the corresponding boronic acid 10 and (iii) Suzuki coupling with the readily prepared acid chloride 8 (average yield 80% per step). For the purpose of additional functionalization, the initially produced TMS-alkyne 11a was desilylated to 11b with K$_2$CO$_3$/MeOH (97%). This last material then afforded alkyne oxazoles 11c-j employing standard coupling methodology.

Upon thermolysis (140-170° C.), alkyne oxazoles 11a-g were converted to variable products (Scheme 3), identified as dienones 12, phenols 13 (R'═H), and the oxidized products 14 and 15 (28-67% combined yields, not optimized). A detailed study of this reaction provided information on the source of each compound. Dienones 12 were the primary reaction products, and they were reasonably stable in the absence of air or acid impurities. On acidic workup, however, dienones 12 underwent equilibration to the corresponding phenols 13 (R'═H), which proved to be extremely sensitive to oxidation even at ambient temperature. This conversion produced directly the tertiary alcohols 14, which on thermolysis gave the quinone methides 15. Unexpectedly, the tautomers 12 survived the reaction conditions and a search of the literature revealed that this phenomenon was common, as for example in various furanoeremophilanes isolated from the *Psacalium* and *Senecio* genera (Gardono-Ramirez, et al. (2001) *J. Nat. Prod.* 64:432; Torres, et al. (1989) *Phytochemistry* 28:3093; Burgueno-Tapia, et al. (2001) *J. Nat. Prod.* 64:518). It is believed that such tautomers are also stabilized by relief of peri-interactions.

Scheme 3

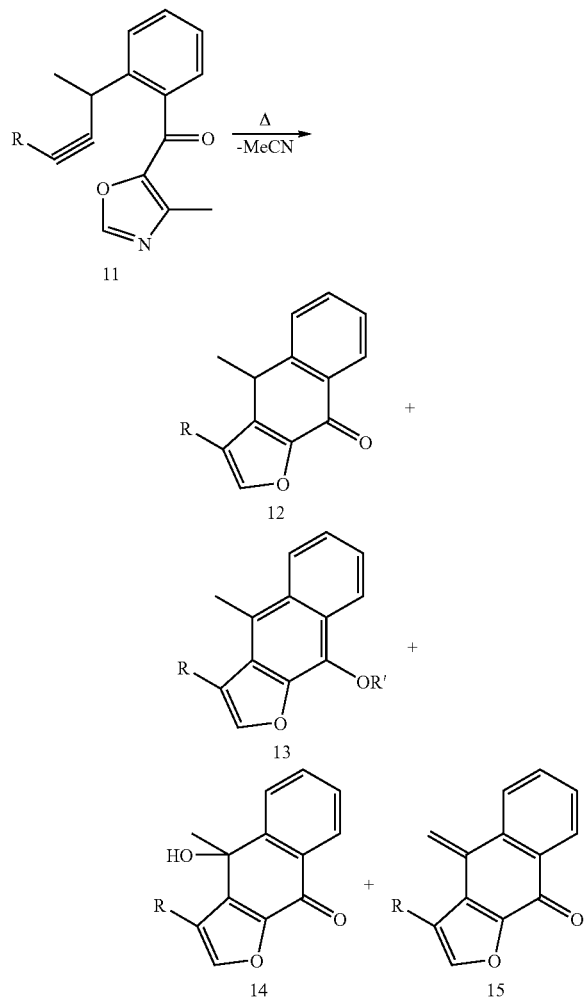

a) R = TMS, b) R = H, C) R = cis-H═CHCO₂Et, d) R = Ph,
e) R = CO₂Et, f) R = CO₂t-Bu, g) R = CO₂Bn, h) R = C(═O)CH₃,
i) R = I, j) R = CH═O.

The structure of 14c was confirmed by X-ray analysis of the corresponding dihydro derivative 16 obtained upon catalytic hydrogenation.

The specific synthetic methods for the synthesis of alkyne oxazoles, and analysis thereof, are as follows. In general, all reactions were performed in flame-dried glassware fitted with rubber septa under positive pressure of nitrogen or argon, unless otherwise noted. Tetrahydrofuran and dichloromethane were passed through activated silica gel under positive pressure of nitrogen prior to use. Triethylamine was distilled from calcium hydride. o-Xylene was distilled from sodium. Acetonitrile (anhydrous, extra dry), toluene (99.8% anhydrous), and dimethylformamide (99.8%, anhydrous) were used as received. TLC was performed on precoated 250 μm silica 60 F254 glass-backed plates. Flash chromatography was performed using $R_f$ grade silica (60 Å, 200-400 mesh) with hexane/EtOAc mixtures as the eluent unless otherwise stated. Melting points are uncorrected. Infrared spectra were recorded on NaCl plates either neat or as thin films prepared with CHCl₃. ¹H and ¹³C NMR spectra were recorded at 300 or 500 MHz. Unless otherwise stated, CDCl₃ was used as the solvent. Resonances are reported in parts per million downfield from TMS and were referenced to either the residual solvent peak (¹H; CHCl₃: δ7.27) or the solvent resonances (¹³C; CDCl₃: δ77.23).

Carbonic acid tert-butyl ester 2-formyl-phenyl ester (4)

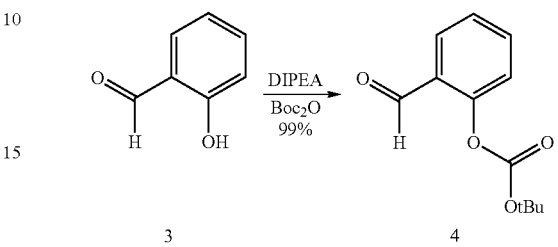

A solution of 45.6 grams (209 mmol, 1.02 eq) of t-butylpyrocarbonate in 205 mL of dry THF was stirred under argon in a dry 500 mL round bottom flask at room temperature. To this colorless solution was sequentially added 0.75 gram (6.1 mmol, 0.03 eq) of N,N-dimethylaminopyridine and 17.8 mL (103 mmol, 0.5 eq) of N,N-diisopropylethylamine. Lastly, 21.8 mL (205 mmol, 1.0 eq) of salicylaldehyde 3 was slowly added (warning: gas evolution) and stirring was continued at room temperature until the reaction was complete by TLC (1:1 hexanes:EtOAc, product $R_f$=0.61). The solution was then diluted with Et₂O and washed with 1.0 M HCl. The aqueous HCl portion was then extracted twice with Et₂O. The combined organic fractions were then washed with brine and dried over MgSO₄. Concentration yields 45.47 grams (99.9%) of the known (Jones, et al. (2001) *J. Org. Chem.* 66(10):3435-3441) aldehyde 4 as a colorless oil, $R_f$ 0.61 (1:1 hexane:EtOAc). ¹H-NMR (500 MHz, CDCl₃): 10.19 (s, 1H), 7.90 (d, J=7.8 Hz, 1H), 7.64 (t, J=7.3 Hz, 1H), 7.41 (t, J=7.5 Hz, 1H), 7.28 (d, 1H), 1.59 (s, 9H).

2-(1-Methyl-3-trimethylsilanyl-prop-2-ynyl)-phenol (6)

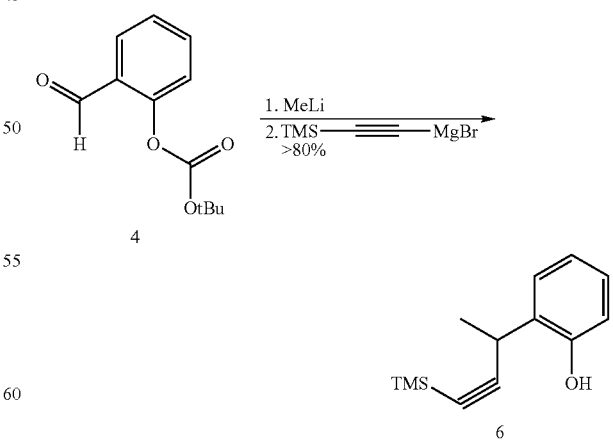

A solution of 18.5 grams (188 mmol, 2.2 eq) of trimethylsilylacetylene in 90 mL of dry THF was stirred under argon in a dry 500 mL round bottom flask at room temperature. To this solution was then slowly added 171 mL (171 mmol of a 1.0 M solution in THF, 2.0 eq) of ethyl magnesium bromide. The colorless solution was stirred for 2 hours. In a separate dry 1 L round bottom flask; 19.0 grams (85.5 mmol, 1.0 eq) of aldehyde 4 was dissolved in 270 mL of dry THF under argon. This solution was then cooled to −78° C. in an acetone/dry ice bath at which time 56.0 mL (89.7 mmol of a 1.6 M solution in Et$_2$O, 1.05 eq) of methyl lithium was added with a syringe pump (2.5 mL/minute) and stirred at −78° C. for 25 minutes. The dry ice bath was then removed and the solution was stirred for 10 minutes at room temperature. The initial Grignard solution from the first flask was then added via cannula to the room temperature 1 L flask and the combined solutions were stirred for 2 hours under argon at room temperature. The solution was then diluted with Et$_2$O and washed sequentially with 1.0 M HCl, saturated NaHCO$_3$, brine and dried over MgSO$_4$. The resulting colorless oil could be purified via silica gel chromatography (hexanes/EtOAc) or used directly in the subsequent step, R$_f$ 0.29 (7:1 hexane:EtOAc). $^1$H-NMR (500 MHz, CDCl$_3$): 7.16 (m, 2H), 6.89 (m, 2H), 6.18 (s, 1H), 3.89 (q, J=7.1 Hz, 1H), 1.51 (d, J=7.3 Hz, 3H), 0.20 (s, 9H). $^{13}$C-NMR (500 MHz, CDCl$_3$): 154.02, 128.56, 128.41, 128.26, 121.15, 117.19, 108.45, 88.53, 29.24, 22.58, 0.16. IR (cm$^{-1}$): 3447 (b), 2959 (w), 2163 (w), 1591 (w), 1453 (m), 1249 (s), 843 (s), 754 (s). HRMS (EI) calcd. for C$_{13}$H$_{18}$OSi: 218.1127. found: 218.1129.

Trifluoromethanesulfonic acid 2-(1-methyl-3-trimethylsilanyl-prop-2-ynyl)-phenyl ester (7)

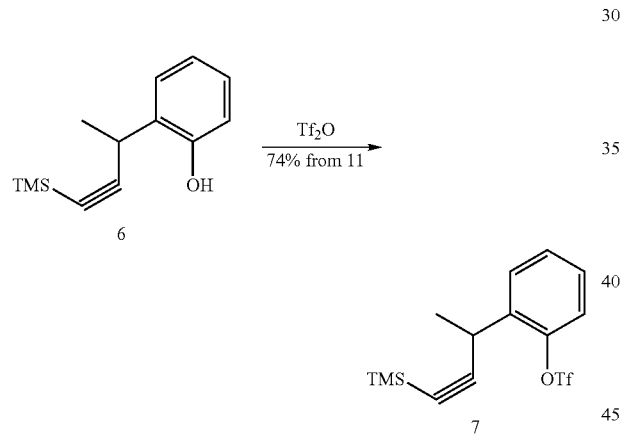

A solution of 20.9 grams (95.7 mmol, 1.0 eq) of phenol 6 in 92.0 mL of CH$_2$Cl$_2$ was stirred in a 250 mL round bottom flask under argon at room temperature. To this colorless solution was then added 580 mg (4.8 mmol, 0.05 eq) of N,N-dimethylaminopyridine followed by 46.0 mL (574 mmol, 6.0 eq) of pyridine. This solution was then cooled to 0° C. in an ice water bath. Once cooled, 19.3 mL (114.8 mmol, 1.2 eq) of Tf$_2$O was carefully added to the cold solution. Once the addition of Tf$_2$O was complete, the ice water bath was removed and the black solution was stirred at room temperature until complete by TLC (7:1 hexane:EtOAc, KMnO$_4$ stain). Upon completion (~30 minutes), the solution was diluted with Et$_2$O and washed with 1.0 M HCl twice, followed by washings with water and brine. The organic fraction was then dried over MgSO$_4$, concentrated and purified via vacuum distillation yielding 24.88 grams (74% for two steps) of a colorless oil, R$_f$ 0.69 (7:1 hexane:EtOAc). $^1$H-NMR (500 MHz, CDCl$_3$): 7.76 (dd, J=7.8 Hz, 1.7 Hz, 1H), 7.41 (dt, J=1.2 Hz, 7.6 Hz, 1H), 7.34 (dt, J=1.7 Hz, 7.8 Hz, 1H), 7.29 (dd, J=1.5 Hz, 8.5 Hz, 1H), 4.14 (q, J=7.1 Hz, 1H), 1.52 (d, J=7.1 Hz, 3H), 0.21 (s, 9H). $^{13}$C-NMR (500 MHz, CDCl$_3$): 146.66, 135.94, 129.88, 128.92, 128.82, 121.33, 118.73 (q, J=320 Hz), 107.57, 87.12, 27.40, 23.56, 0.21. $^{19}$F-NMR (500 MHz, CDCl$_3$): −74.37. IR (cm$^{-1}$): 2960 (w), 2169 (w), 1757 (w), 1422 (s), 1214 (s), 1142 (s), 886 (s), 844 (s), 761 (m). HRMS (EI) calcd. for C$_{14}$H$_{17}$F$_3$O$_3$SSi: 350.0620. found: 350.0619.

4,4,5,5-Tetramethyl-2-[2-(1-methyl-3-trimethylsilanyl-prop-2-ynyl)-phenyl]-[1,3,2]dioxaborolane (9)

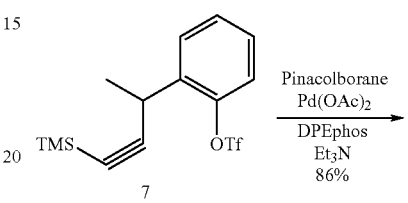

A mixture of 547 mg (2.44 mmol, 0.03 eq) of Pd(OAc)$_2$ and 2.63 grams (4.88 mmol, 0.06 eq) of bis[2-(diphenylphosphino)phenyl]ether (DPEphos) was stirred in 163 mL of dioxane in a 500 mL round bottom flask under argon at room temperature. To this heterogenous mixture was sequentially added 22.7 mL (163 mmol, 2.0 eq) of Et$_3$N and 28.5 grams (81.3 mmol, 1.0 eq) of triflate 7. Lastly, 17.6 mL (122 mmol, 1.5 eq) of 4,4,5,5-Tetramethyl-1,3,2-dioxaborolane was added and the mixture was sparged with argon for 10 minutes. The reaction was then heated to 60° C. in a silicon oil bath and stirred until complete by $^1$H-NMR (aliquots removed periodically). Upon completion (~19 hours) the mixture was cooled to room temperature and diluted with Et$_2$O. The solution was then washed with water and the water layer was back extracted with Et$_2$O. The combined Et$_2$O layers were washed with brine and dried over MgSO$_4$. Concentration and silica gel chromatography (hexane/EtOAc) gave 23.1 grams (86%) of 9 as a yellow oil, R$_f$ 0.64 (1:1 hexane:EtOAc). $^1$H-NMR (500 MHz, CDCl$_3$): 7.81 (1H, d, J=7.1 Hz), 7.75 (1H, d, J=7.8 Hz), 7.47 (1H, d, J=7.6 Hz), 7.24 (1H, d, J=7.4 Hz), 4.73 (1H, q, J=7.1 Hz), 1.45 (3H, d, J=7.1 Hz), 1.36 (6H, s), 1.35 (6H, s), 0.215 (9H, s). $^{13}$C-NMR (500 MHz, CDCl$_3$): 150.25, 136.35, 131.64, 126.85, 125.94, 111.34, 85.66, 83.77, 31.52, 26.29, 25.17, 24.93, 0.45. IR (cm$^{-1}$): 2975 (m), 2165 (m), 1598 (m), 1441 (m), 1380 (m), 1346 (s), 1249 (m), 1145 (m), 842 (s) HRMS (EI) calcd. for $C_{19}H_{29}BO_2Si$: 328.2030. found: 328.2028.

2-(1-Methyl-3-trimethylsilanyl-prop-2-ynyl)-phenyl-boronic acid (10)

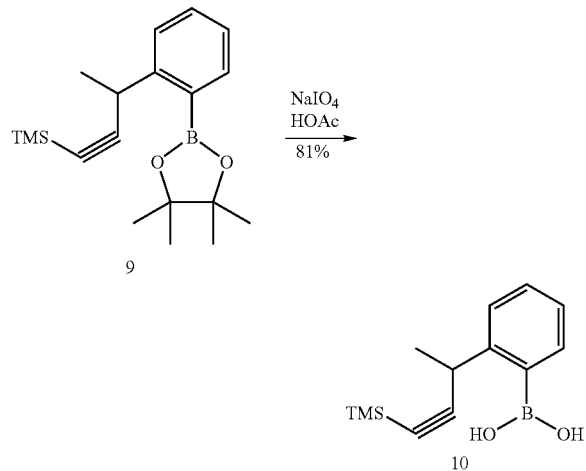

A mixture of 13.93 grams (42.4 mmol, 1.0 eq) of boronate 9 and 27.2 grams (127 mmol, 3.0 eq) of $NaIO_4$ in 126 mL of dry THF was stirred in a 250 mL round bottom flask at room temperature. To this heterogenous mixture was added 42 mL of AcOH (0.5 M). The mixture was warmed to 45° C. and stirred vigorously until complete by TLC (1:1 hexanes:EtOAc). Upon completion (~65 hours) the mixture was diluted with $CH_2Cl_2$ and washed with $H_2O$. The aqueous layer was extracted twice more with $CH_2Cl_2$ and the combined organic layers were washed with aqueous $Na_2S_2O_3$ and then dried over $MgSO_4$. After concentration, the product was purified by filtering through a plug of silica gel with hexane (elutes impurities) followed by EtOAc (elutes product) to give 8.56 grams (81%) of 10 as a colorless oil which is a mixture of boronate esters, $R_f$ 0.20-0.50 (1:1 hexane:EtOAc). $^1$H-NMR (500 MHz, $CDCl_3$): 8.19 (1H, m), 7.82 (1H, m), 7.61 (1H, m), 7.41 (1H, m), 4.96 (1H, m), 1.64 (3H, m), 0.19 (9H, m). $^{13}$C-NMR (500 MHz, $CDCl_3$): 151.45, 137.26, 132.98, 127.65, 126.45, 111.05, 85.85, 31.43, 25.84, 0.41. IR (cm$^{-1}$): 2961 (w), 2164 (w), 1597 (w), 1442 (m), 1345 (s), 1248 (m), 915 (w), 842 (s), 759 (m), 701 (w). HRMS (EI) calcd. for $C_{13}H_{19}BO_2Si$: 246.1247. found: 245.1173 (M-1).

(4-Methyl-oxazol-5-yl)-[2-(1-methyl-3-trimethylsilanyl-prop-2-ynyl)-phenyl]-methanone (11a)

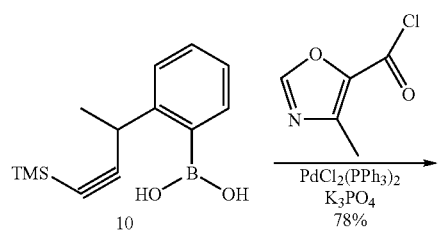

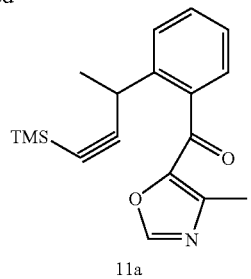

11a

A solution of 840 mg (1.2 mmol, 0.05 eq) of $PdCl_2(PPh_3)_2$ in 60 mL of dry toluene was stirred in a 200 mL 3-necked flask equipped with a mechanical stirrer at room temperature under argon. To this mixture was sequentially added 5.90 grams (23.96 mmol, 1.0 eq) of boronic acid 10 and 3.81 grams (26.36 mmol, 1.1 eq) of 4-Methyl-oxazole-5-carbonyl chloride 8. Lastly, 11.0 grams (47.92 mmol, 2.0 eq) of finely powdered $K_3PO_4 \cdot H_2O$ was added to the flask. The heterogenous mixture was stirred vigorously with the mechanical stirrer and warmed to 60° C. The solution was stirred at this temperature until complete by TLC (1:1 hexane:EtOAc). The reaction rate was highly dependent on the rate of stirring. Upon completion (~2 hours) the reaction was cooled to room temperature and the dark mixture was passed through a pad of CELITE. The CELITE was washed with EtOAc and the combined organic fractions were then washed with water and the aqueous layer was back extracted with EtOAc. The combined EtOAc extracts were washed with brine and dried over $MgSO_4$. After concentration, silica gel chromatography (hexane/EtOAc) gave 5.85 grams (78%) of 11a as a brown oil, $R_f$ 0.56 (1:1 hexane:EtOAc). $^1$H-NMR (500 MHz, $CDCl_3$): 7.91 (1H, s), 7.75 (1H, d, J=7.8 Hz), 7.53 (1H, m), 7.37 (2H, m), 4.14 (1H, q, J=7.1 Hz), 2.36 (3H, s), 1.50 (3H, d, J=7.1 Hz), 0.11 (9H, s). $^{13}$C-NMR (500 MHz, $CDCl_3$): 185.52, 152.11, 146.91, 145.45, 142.46, 136.31, 131.69, 128.54, 128.24, 126.55, 109.40, 86.21, 29.60, 24.72, 14.18, 0.22. IR (cm$^{-1}$): 2957 (m), 2164 (m), 1655 (s), 1579 (s), 1354 (m), 1248 (s), 904 (s), 843 (s), 760 (s). HRMS (EI) calcd. for $C_{18}H_{21}NO_2Si$: 311.1342. found 311.1356.

4-Methyl-oxazole-5-carboxylic acid

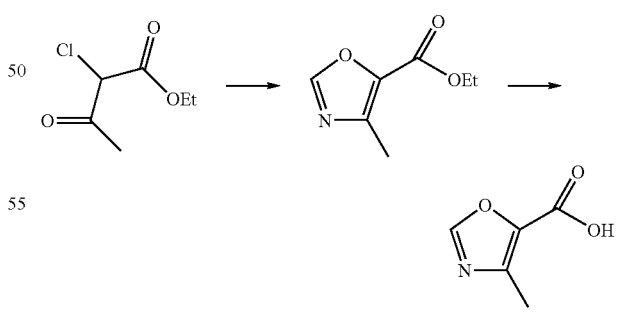

A solution of 40.0 grams (0.243 mol, 1.0 eq) of 2-Chloro-3-oxo-butyric acid ethyl ester in 240 mL formic acid (99%) was stirred at room temperature in a 500 mL round bottom flask equipped with a $H_2O$ condenser. To this solution was added 80.0 grams (1.27 mmol, 5.2 eq) of ammonium formate. The solution was then heated to reflux for five hours. After cooling to room temperature, the solution was diluted with water (1 L) and neutralized with $Na_2CO_3$. The aqueous solution was then extracted three times with $Et_2O$ and the combined organic fractions were dried over $MgSO_4$. After concentration, vacuum distillation (~10 mmHg, b.p. 53° C.-61° C.) gave a mixture of starting material and 4-Methyl-oxazole-5-carboxylic acid ethyl ester as a colorless oil (21.7 grams). This mixture was dissolved in 100 mL of aqueous sodium hydroxide (2 N) and refluxed for 1 minute. The reaction was then poured onto ice and acidified with concentrated HCl and the known (Sen & Sengupta (1985) *Ind. J. Chem. Section B: Org. Chem. Including Med. Chem.* 24B(5):535-8) free acid precipitated as a white solid (6.04 grams, 20% overall yield) Mp: 241.4-242.6° C.

4-Methyl-oxazole-5-carbonyl chloride (8)

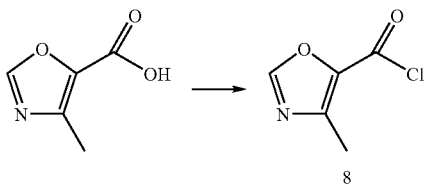

A heterogenous mixture of 3.00 grams (23.6 mmol, 1.0 eq) of 4-Methyl-oxazole-5-carboxylic acid in 109 mL of dry $CH_2Cl_2$ was stirred in a 250 mL round bottom flask under argon at room temperature. To this mixture was added 23.6 mL (2.0 M in $CH_2Cl_2$, 2.0 eq) of oxalyl chloride. Lastly, 90 μL of DMF was added and the mixture was stirred vigorously at room temperature until homogenous (~9 hours). The mixture was then concentrated and purified with a short silica column to give 3.2 grams (94%) of the known (Sen & Sengupta (1985) supra) 8 as a colorless oil. $^1$H-NMR (500 MHz, $CDCl_3$): 8.00 (s, 1H), 2.57 (s, 3H).

(4-Methyl-oxazol-5-yl)-[2-(1-methyl-prop-2-ynyl)-phenyl]-methanone (11b)

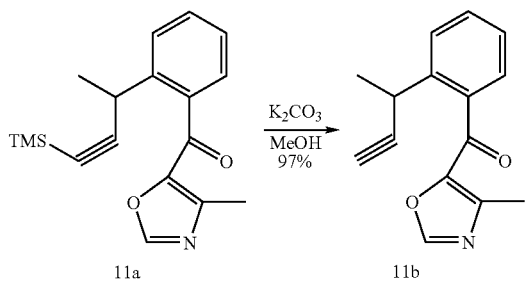

A solution of 1.16 grams (3.72 mmol, 1.0 eq) of oxazole 11a in 19 mL of MeOH was stirred in a 50 mL round bottom flask at room temperature under argon. To this solution was added 1.54 grams (11.16 mmol, 3.0 eq) of $K_2CO_3$ forming a heterogenous mixture. This suspension was vigorously stirred at room temperature until the reaction was complete by TLC (1:1 hexane:EtOAc, $R_f$=0.50). Upon completion (~1 hour), the mixture was diluted with EtOAc and washed with 1.0 M HCl. The aqueous layer was then extracted twice more with EtOAc and the combined organic fractions were washed with brine and dried over $MgSO_4$. Concentration yielded 860 mg (97%) of 11b as a light brown oil. This material could be purified via silica gel chromatography (hexane/EtOAc), though often the material was used directly for subsequent transformations. $^1$H-NMR (500 MHz, $CDCl_3$): 7.91 (s, 1H), 7.78 (1H, d, J=7.8 Hz), 7.54 (1H, t, J=7.6 Hz), 7.40 (1H, d, J=7.6 Hz), 7.35 (1H, t, J=7.6 Hz), 4.12 (1H, dq, J=7.0 Hz, 2.5 Hz), 2.38 (3H, s), 2.18 (1H, d, J=2.4 Hz), 1.51 (3H, d, J=6.8 Hz). $^{13}$C-NMR (500 MHz, $CDCl_3$): 185.43, 152.17, 147.06, 145.38, 142.10, 136.17, 131.80, 128.50, 128.32, 126.68, 87.10, 70.17, 28.31, 24.65, 14.16. IR (cm$^{-1}$): 3293 (w), 1653 (vs), 1579 (s), 1485 (m), 1443 (w), 1384 (m), 1356 (s), 907 (s). HRMS (EI) calcd. for $C_{15}H_{13}NO_2$: 239.0946. found: 239.0936.

6-[2-(4-Methyl-oxazole-5-carbonyl)-phenyl]-hept-2-en-4-ynoic acid ethyl ester (11c)

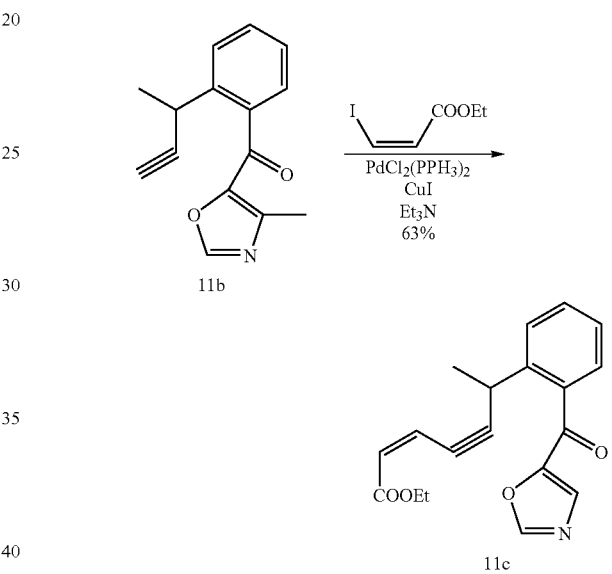

A solution of 300 mg (1.25 mmol, 1.0 eq) of alkyne 11b in 3.0 mL of dry THF was stirred in a 10 mL round bottom flask at room temperature under argon. To this solution was added 650 μL (3.75 mmol, 5.0 eq) of N,N-diisopropylethylamine followed by 340 mg (1.50 mmol, 1.2 eq) of 3-Iodo-acrylic acid ethyl ester. This solution was then sparged with argon for 10 minutes, at which point 44 mg (0.063 mmol, 0.05 eq) of $PdCl_2(PPh_3)_2$ and 12 mg (0.063 mmol, 0.05 eq) of CuI were added at once and the solution was stirred at room temperature until the reaction was complete by TLC (3:1 hexane:acetone, $R_f$=0.30). Upon completion (~4 hours) the reaction was diluted with EtOAc and washed with 1.0 M HCl. The aqueous layer was then extracted twice with EtOAc. The combined organic fractions were then washed with saturated $NaHCO_3$ and brine and then dried over $MgSO_4$. Purification via silica gel flash chromatography (hexane/EtOAc) yielded 252 mg (63%) of 11c as a pale brown oil, $R_f$ 0.47 (1:1 hexane:EtOAc). $^1$H-NMR (500 MHz, $CDCl_3$): 7.92 (1H, s), 7.87 (1H, d, J=7.9 Hz), 7.56 (1H, dt, J=7.8 Hz, 1.2 Hz), 7.41 (1H, d, J=7.6 Hz), 7.35 (1H, t, J=7.6 Hz), 6.11 (1H, dd, J=11.5 Hz, 2.4 Hz), 6.04 (1H, d, J=11.5 Hz), 4.35 (1H, dq, J=7.1 Hz, 2.2 Hz), 4.21 (2H, q, J=7.1 Hz), 2.39 (3H, s), 1.57 (3H, d, J=7.1 Hz), 1.27 (3H, t, J=7.1 Hz). $^{13}$C-NMR (500 MHz, $CDCl_3$): 185.43, 164.92, 152.18, 147.04, 145.37, 142.09, 136.11, 131.86, 129.00, 128.44, 128.35, 126.69, 123.28, 105.40, 79.35, 60.52, 29.88, 24.64, 14.42, 14.18. IR (cm$^{-1}$): 2976 (m), 2213 (w), 1719 (s), 1653 (s), 1603 (m), 1579 (s), 1384 (m), 1355 (m), 1291 (m), 1183 (vs), 905 (s). HRMS (EI) calcd. for $C_{20}H_{19}NO_4$: 337.1314. found: 337.1322.

(4-Methyl-oxazol-5-yl)-[2-(1-methyl-3-phenyl-prop-2-ynyl)-phenyl]-methanone (11d)

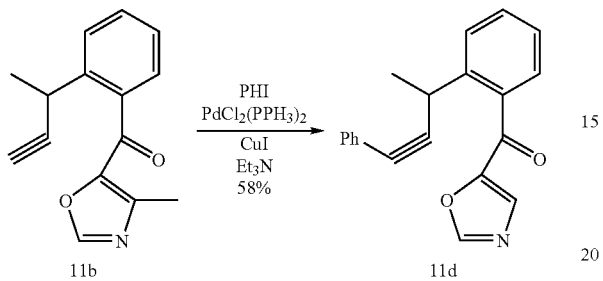

A solution of 40.0 mg (0.167 mmol, 1.0 eq) of alkyne 11b in 750 μL of dry $Et_3N$ was stirred in a 5 mL round bottom flask at room temperature under argon. To this solution was then added 23 μL (0.20 mmol, 1.2 eq) of iodobenzene. The resulting solution was sparged with argon for 5 minutes, at which time 6.0 mg (0.008 mmol, 0.05 eq) of $PdCl_2(PPh_3)_2$ and 1.5 mg (0.008 mmol, 0.05 eq) of CuI were added and the reaction was stirred at room temperature until complete by TLC (1:1 hexane:EtOAc, $R_f$=0.42). Upon completion (~5 hours) the solution was diluted with $Et_2O$ and washed sequentially with 1.0 M HCl and $H_2O$. The organic fraction was then dried over $MgSO_4$, concentrated and purified via silica gel chromatography (hexane/EtOAc) to give 44 mg (83%) of 11d as a pale brown oil, $R_f$ 0.42 (1:1 hexane:EtOAc). $^1$H-NMR (500 MHz, $CDCl_3$): 7.89 (1H, s), 7.82 (1H, d, J=7.3 Hz), 7.57 (1H, dt, J=7.8 Hz, 1.9 Hz), 7.42 (1H, m), 7.38 (1H, m), 7.34 (2H, m), 7.28 (3H, m), 4.34 (1H, q, J=7.1 Hz), 2.37 (3H, s), 1.62 (3H, d, 7.1 Hz). $^{13}$C-NMR (500 MHz, $CDCl_3$): 185.67, 152.11, 146.95, 145.47, 142.66, 136.49, 131.69, 131.68, 128.64, 128.37, 128.19, 128.07, 126.62, 123.55, 92.70, 82.47, 29.37, 24.61, 14.18. IR (cm$^{-1}$): 1653 (vs), 1579 (s), 1487 (m), 1442 (w), 1384 (m), 1355 (m), 900 (m), 757 (s). HRMS (EI) calcd. for $C_{21}H_{17}NO_2$: 315.1259. found: 315.1244.

Example 2

Synthesis of Viridin Model

Toward the synthesis of a viridin model, two approaches were employed. In the first of these, the alkyne oxazole 11c (R=cis-HC=CHCO$_2$Et; Scheme 3) was employed. Alkyne oxazole 11c was prepared in 65% yield by Sonogashira coupling of 11b (R=H) with ethyl cis-iodoacrylate. Upon heating in o-xylene (140° C.), 11c was transformed to a mixture of 12c-15c, in a combined yield of 59% at 73% conversion (Scheme 3). The formation of 14c and 15c could be somewhat lessened by thorough degassing and employing antioxidants. In general, though, it was expeditious to allow oxidation to proceed, since both 14c and 15c functioned as convenient and stable sources of the parent phenol 13 and related derivatives. For example, employing 14c allowed for the preparation of the saturated ester derivative 17 by a simple two step sequence including catalytic hydrogenation (14c→16; the structure of 14c was confirmed by X-ray analysis of the dihydro derivative 16 obtained upon catalytic hydrogenation), followed by regeneration of the parent phenol ($Et_3SiH$, $BF_3Et_2O$) and in situ silylation (Scheme 4). The identical sequence was applicable with equal efficiency to mixtures of 14c and 15c. DIBAH reduction of 17 then afforded a nearly quantitative yield of aldehyde 18, which was a suitable substrate for testing the formation of ring A.

In the second approach, ester 17 was prepared in higher overall yield from furanoester 13e by 1) DIBAH reduction to aldehyde 13j; 2) Wittig reaction to give unsaturated ester 13c; and 3) catalytic hydrogenation to give 17.

Subsequently, 18 cleanly underwent the desired ring closure, producing with $TiCl_4/CH_2Cl_2$ a 75% yield of viridin models 19S and 19A with 4:1 stereoselectivity (Scheme 4). Under these conditions no evidence was found for equilibration between 19S and 19A.

Scheme 4

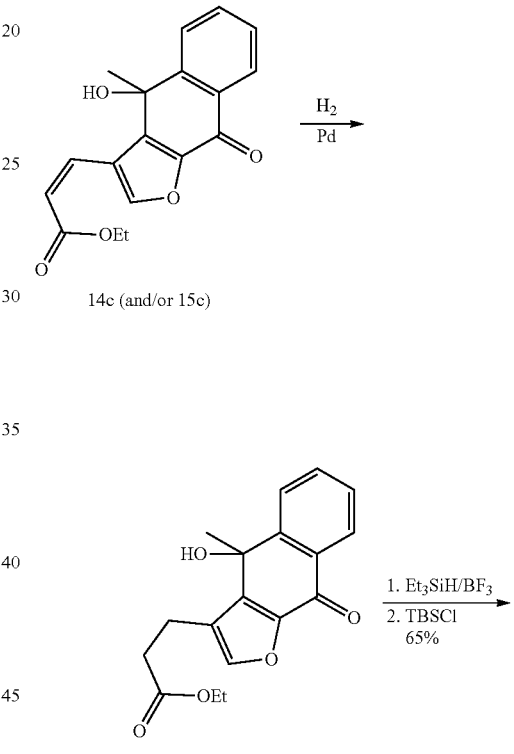

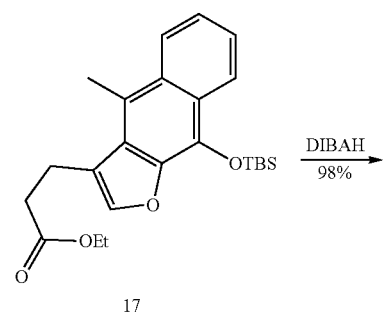

-continued

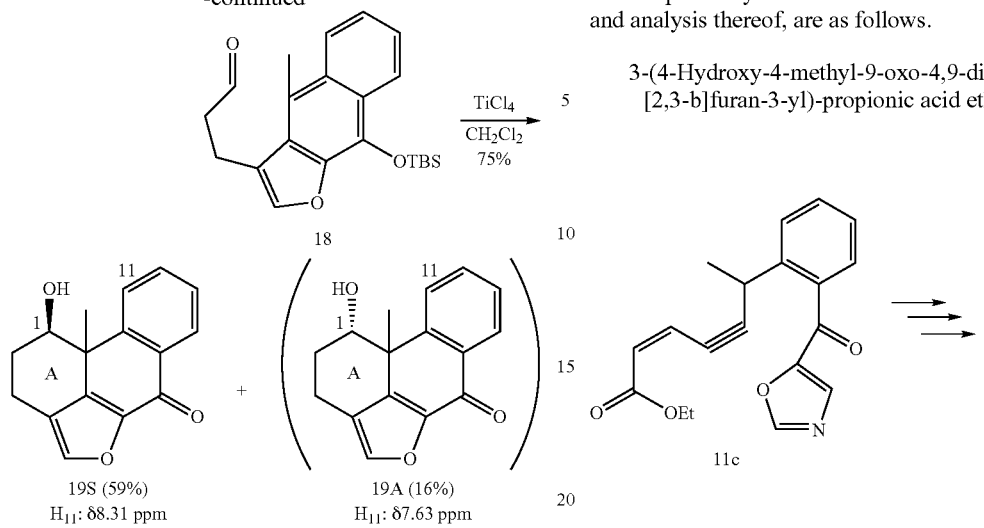

Care was taken in assigning the structures of 19S and 19A. In addition to detailed NOE studies, which fully corroborated the structure of 19S, the isomeric alcohols 19S and 19A had a tell-tale signature in their NMR spectra. As in viridin (1), $H_{11}$ in 19S resides in the deshielding zone of the $C_1$-hydroxyl group (nearly co-planar), and its signal was shifted dramatically downfield (8.31 ppm). In contrast, the corresponding signal in 19A was found at 7.63 ppm. A nearly identical chemical shift difference was observed for $H_{11}$ in the closely related epimeric alcohols 20S and 20A, prepared by Anderson et al. ((2004) supra) in the synthesis of viridin 1. The conversion of 18 to 19S can also be optimized to both higher yields and selectivities.

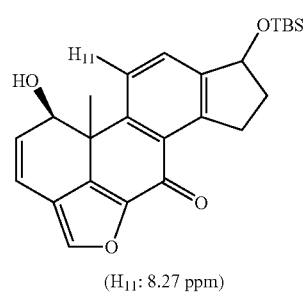

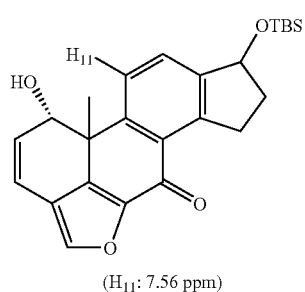

The specific synthetic methods for the synthesis of viridin, and analysis thereof, are as follows.

3-(4-Hydroxy-4-methyl-9-oxo-4,9-dihydro-naphtho [2,3-b]furan-3-yl)-propionic acid ethyl ester (16)

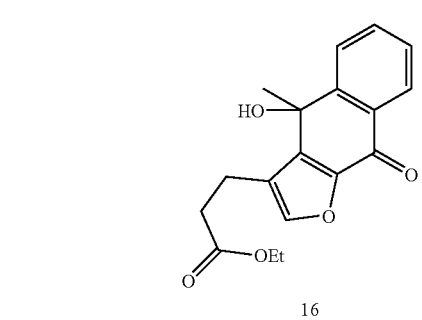

A solution of 1.16 grams (3.44 mmol) of oxazole 11c in 69 mL of dry o-xylene was stirred in a 250 mL round bottom flask at room temperature under argon. The solution was then thoroughly degassed via three freeze/pump/thaw cycles. The degassed solution was then heated to reflux for 12 hours under an argon atmosphere. It was found that extended reaction times at high temperatures led to significant decomposition. After cooling to room temperature, the solution was passed through a plug of silica gel with hexane to elute the o-xylene. The products were then eluted from the silica gel with EtOAc and the crude brown oil was purified via silica gel chromatography (hexane/EtOAc) to give 309 mg (27%) of recovered starting material 11c and 569 mg (~45%) of a mixture of Diels-Alder products (12c, 14c, 15c) as a brown oil. This mixture was then dissolved in 10 mL of THF containing 1.0 M HCl (5 drops) and stirred for 4 hours at room temperature to tautomerize/oxidize the keto-tautomer 12c. The solution was diluted with $CH_2Cl_2$ and washed with brine. The aqueous layer was then extracted twice more with $CH_2Cl_2$ and the combined organic fractions were dried over $MgSO_4$ and concentrated. This crude binary mixture (14c, 15c) was then dissolved in 17 mL of MeOH and stirred at room temperature. To this solution was added 85 mg of Pd/C (10%) and the solution was stirred vigorously under a hydrogen atmosphere for 4 hours. The solution was then filtered through CELITE and purified via silica gel chromatography (hexane/EtOAc) to give 218 mg (27% overall) of saturated ester 16 as a colorless solid, $R_f$ 0.44 (1:1 hexane:EtOAc). Mp: 103.5-103.8° C. $^1$H-NMR (500 MHz, CDCl$_3$): 7.96 (1H, d, J=7.8 Hz), 7.80 (1H, d, J=7.7 Hz), 7.58 (1H, t, J=7.6 Hz), 7.37 (1H, s), 7.35 (1H, t, J=7.3 Hz), 4.10 (2H, q, J=7.1 Hz), 3.78 (1H, s), 3.09 (1H, m), 2.97 (1H, m), 2.72 (2H, t, J=7.0 Hz), 1.72 (3H, s), 1.22 (3H, t, J=7.1 Hz). $^{13}$C-NMR (500 MHz, CDCl$_3$): 173.17, 173.14, 149.74, 146.13, 145.35, 141.34, 133.35, 129.96, 128.11, 126.61, 126.57, 124.80, 69.79, 60.96, 34.33, 31.59, 19.06, 14.35. IR (cm$^{-1}$): 3224 (b), 2982 (w), 1730 (s), 1687 (vs), 1596 (m), 1529 (w), 1458 (m), 1415 (s), 1372 (m), 1228 (s), 1190 (s), 906 (m). Anal. Calcd. for C$_{18}$H$_{18}$O$_5$: C, 68.78; H, 5.77. Found: C, 68.47; H, 5.94. Structure confirmed by X-Ray.

Data Collection. A crystal (approximate dimensions 0.40× 0.20×0.04 mm$^3$) was placed onto the tip of a 0.1 mm diameter glass capillary and mounted on a SIEMENS SMART Platform CCD diffractometer for a data collection at 173(2) K (SMART V5.054, Bruker Analytical X-ray Systems, Madison, Wis. (2001)). A preliminary set of cell constants was calculated from reflections harvested from three sets of 20 frames. These initial sets of frames were oriented such that orthogonal wedges of reciprocal space were surveyed. This produced initial orientation matrices determined from 44 reflections. The data collection was carried out using MoKα radiation (graphite monochromator) with a frame time of 30 seconds and a detector distance of 4.9 cm. A randomly oriented region of reciprocal space was surveyed to the extent of one sphere and to a resolution of 0.77 Å. Three major sections of frames were collected with 0.30° steps in ω at three different φ settings and a detector position of −28° in 2θ. The intensity data were corrected for absorption and decay (SADABS; Blessing (1995) Acta Cryst. A51:33-38). Final cell constants were calculated from the xyz centroids of 2504 strong reflections from the actual data collection after integration (SAINT; SAINT+ V6.45, Bruker Analytical X-Ray Systems, Madison, Wis. (2003)).

Structure Solution and Refinement. The structure was solved using SHELXS-97 (SHELXTL V6.14, Bruker Analytical X-Ray Systems, Madison, Wis. (2000)) and refined using SHELXL-97 (SHELXTL V6.14, Bruker Analytical X-Ray Systems, Madison, Wis. (2000)). The space group P2$_1$/c was determined based on systematic absences and intensity statistics. A direct-methods solution was calculated which provided most non-hydrogen atoms from the E-map. Full-matrix least squares/difference Fourier cycles were performed which located the remaining non-hydrogen atoms. All non-hydrogen atoms were refined with anisotropic displacement parameters. The proton on O5 was found from the difference map and refined with anisotropic displacement parameters. All remaining hydrogen atoms were placed in ideal positions and refined as riding atoms with relative isotropic displacement parameters. The final full matrix least squares refinement converged to R1=0.0503 and wR2=0.1365 (F$^2$, all data).

Structure Description. The structure is the one suggested. The addition of the hydroxyl group at C6 results in a chiral molecule. However, since the molecule crystallized in the centrosymmetric space group P2$_1$/c, the sample was identified as a racemic mixture. The different enantiomers were hydrogen bonded to each other through O5 and O2.

3-[9-(tert-Butyl-dimethyl-silanyloxy)-4-methyl-naphtho[2,3-b]furan-3-yl]-propionic acid ethyl ester (17)

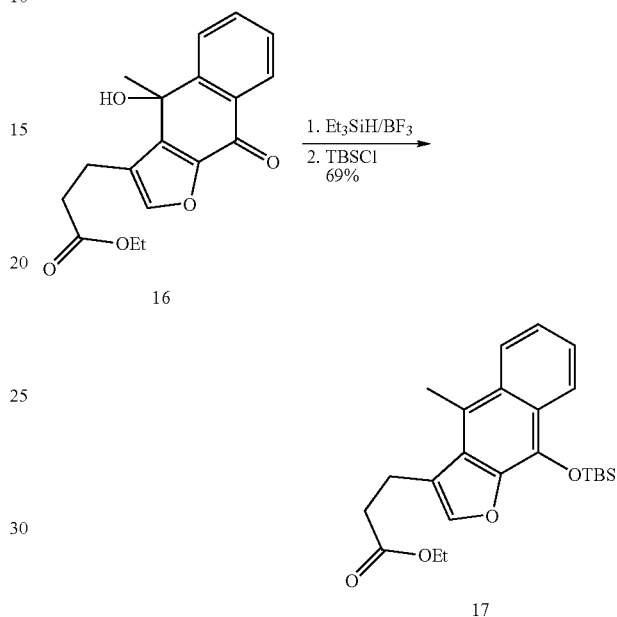

A solution of 24.0 mg (0.076 mmol, 1.0 eq) of alcohol 16 in 5.0 mL of dry CH$_2$Cl$_2$ was stirred in a 5 mL round bottom flask at room temperature under argon. To this solution was added 36.6 μL of Et$_3$SiH (0.229 mmol, 3.0 eq). The solution was then cooled to 0° C. in an ice water bath. After cooling, 28.0 μL (0.220 mmol, 2.9 eq) of BF$_3$-Et$_2$O was slowly added and the resulting solution was stirred until all the starting material was consumed by TLC (1:1 hexane:EtOAc, R$_f$=0.56). After alcohol 16 was completely consumed (~15 minutes), 69.0 mg (0.456 mmol, 6.0 eq) of TBSCl and 31.0 mg (0.456 mmol, 6.0 eq) of imidazole were added at once and the ice water bath was removed. The solution was then stirred at room temperature until the reaction was complete by TLC (1:1 hexane:EtOAc, R$_f$=0.80). Upon completion (~18 hours) the solution was diluted with CH$_2$Cl$_2$ and washed with a saturated aqueous NH$_4$Cl solution. The aqueous layer was then extracted twice with CH$_2$Cl$_2$ and the combined organic fractions were dried over MgSO$_4$ and concentrated. Silica gel chromatography (hexane/EtOAc) yielded 116 mg (69%) of 17 as a colorless solid, R$_f$ 0.80 (1:1 hexane:EtOAc). Mp: 92.4-93.5° C. $^1$H-NMR (500 MHz, CDCl$_3$): 8.31 (1H, m), 8.10 (1H, m), 7.47 (3H, m), 4.20 (2H, q, J=7.1 Hz), 3.29 (2H, t, J=7.6 Hz), 2.93 (3H, s), 2.78 (2H, t, J=7.7 Hz), 1.28 (3H, t, J=7.2 Hz), 1.15 (9H, s), 0.27 (6H, s). $^{13}$C-NMR (500 MHz, CDCl$_3$): 172.93, 143.40, 143.25, 132.82, 130.16, 127.98, 125.74, 124.02, 123.87, 123.69, 122.69, 119.97, 118.53, 60.84, 34.56, 26.24, 21.79, 18.93, 14.45, 14.42, −3.86. IR (cm$^{-1}$): 2960 (m), 2854 (w), 1740 (vs), 1630 (w), 1461 (m),

3-[9-(tert-Butyl-dimethyl-silanyloxy)-4-methyl-naphtho[2,3-b]furan-3-yl]-propionaldehyde (18)

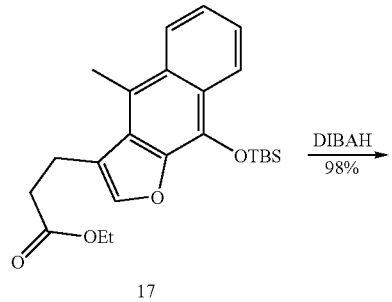

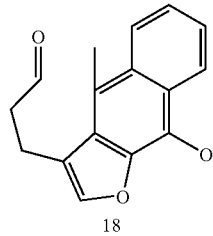

A solution of 67.0 mg (0.162 mmol, 1.0 eq) of ester 17 in 1.60 mL of dry CH$_2$Cl$_2$ was stirred in a dry 5 mL round bottom flask at room temperature under argon. The solution was then cooled to −78° C. in a dry ice/acetone bath. Once cooled, 162 μL (1.2 M in toluene, 0.195 mmol, 1.2 eq) of Diisobutylaluminum hydride was added dropwise and the resulting solution was stirred at −78° C. for 30 minutes. While still cold, the solution was then quenched via the dropwise addition of 170 μL of MeOH followed by 670 μL of saturated aqueous sodium potassium tartrate (Rochelle's salt) added at once. The dry ice/acetone bath was then removed and the solution was diluted with Et$_2$O and stirred for 20 minutes. The colorless solution was then filtered through CELITE. The CELITE was washed with Et$_2$O and the combined organic fractions were washed with brine. The aqueous layer was further extracted with Et$_2$O and the combined organic fractions were dried over MgSO$_4$. Concentration yielded 58.8 mg (98%) of 18 as a colorless solid, R$_f$ 0.72 (1:1 hexane:EtOAc). Mp: 152.5-153.6° C. $^1$H-NMR (500 MHz, CDCl$_3$): 9.92 (1H, s), 8.31 (1H, m), 8.09 (1H, m), 7.47 (2H, m), 7.44 (1H, s), 3.29 (2H, t, J=7.3 Hz), 2.93 (2H, t, J=7.4 Hz), 2.91 (3H, s), 1.15 (9H, s), 0.27 (6H, s). $^{13}$C-NMR (500 MHz, CDCl$_3$): 201.35, 143.46, 143.26, 130.19, 127.88, 125.80, 124.12, 123.86, 123.79, 122.72, 119.76, 118.44, 43.76, 26.24, 18.93, 18.85, 14.45, −3.85. IR (cm$^{-1}$): 2927 (m), 2856 (m), 1724 (s), 1628 (m), 1461 (m), 1390 (s), 1247 (m), 1191 (m), 1117 (s), 988 (s), 826 (s), 786 (s), 760 (s). Anal. Calcd. for C$_{22}$H$_{28}$O$_3$Si: C, 71.70; H, 7.66. Found: C, 71.34; H, 7.68.

1-Hydroxy-10b-methyl-1,2,3,10b-tetrahydro-5-oxa-acephenanthrylen-6-one (19)

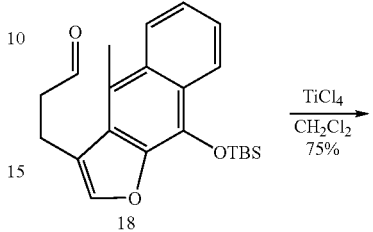

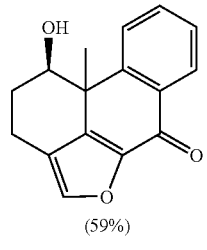

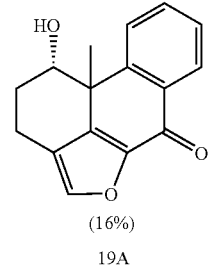

A solution of 50.0 mg (0.136 mmol, 1.0 eq) of aldehyde 18 in 13.6 mL of dry CH$_2$Cl$_2$ was stirred in a 25 mL round bottom flask at room temperature under argon. To this solution was slowly added 271 μL (1.0 M in CH$_2$Cl$_2$, 0.271 mmol, 2.0 eq) of TiCl$_4$. The resulting dark green solution was stirred for 45 minutes (extended reaction times were found to cause decomposition). The solution was then diluted with CH$_2$Cl$_2$ and washed with H$_2$O. The aqueous portion was then extracted three times with CH$_2$Cl$_2$. The combined organic fractions were then dried over MgSO$_4$ and concentrated. Purification via silica gel chromatography (hexane/EtOAc) gave 20.4 mg (59%) of the syn-isomer 19-Syn and 5.4 mg (16%) of the anti-isomer 19-Anti as unstable brown oils. Neither isomer was stable at room temperature for prolonged periods, though they are stable in a refrigerator for several weeks. The decomposition was of a general nature and none of the stable, known retro-aldol product was observed.

Syn-isomer 19-Syn: R$_f$ 0.25 (1:1 hexane:EtOAc). $^1$H-NMR (500 MHz, CDCl$_3$): 8.35 (d, J=7.8 Hz, 1H), 8.32 (d, J=8.7 Hz, 1H), 7.53 (t, J=7.5 Hz, 1H), 7.45 (s, 1H), 7.43 (t, J=7.5 Hz, 1H), 4.13 (dd, J=4.9 Hz, 10.7 Hz, 1H), 2.95 (dd, J=8.8 Hz, 17.1 Hz, 1H), 2.78 (m, 1H), 2.29 (m, 1H), 2.20 (m, 1H), 1.95 (bs, 1H), 1.55 (s, 3H). $^{13}$C-NMR (500 MHz, CDCl$_3$): 172.85, 149.61, 145.93, 145.22, 143.62, 133.32, 132.28, 128.40, 127.88, 127.17, 120.97, 72.57, 41.47, 29.37, 25.69, 17.14. IR (cm$^{-1}$): 3420 (b), 2929 (w), 1657 (vs), 1596 (m), 1453 (m), 1233 (w), 1012 (m), 913 (m). HRMS (EI) calcd. for C$_{16}$H$_{14}$O$_3$: 254.0943. found: 254.0942.

Anti-isomer 19-Anti: $R_f$ 0.15 (1:1 hexane:EtOAc). $^1$H-NMR (500 MHz, CDCl$_3$): 8.41 (d, J=7.3 Hz, 1H), 7.62 (m, 2H), 7.55 (s, 1H), 7.48 (m, 1H), 4.76 (t, J=2.9 Hz, 1H), 2.84 (dd, J=4.9 Hz, 9.3 Hz, 2H), 2.41 (dtd, J=2.4 Hz, 9.3 Hz, 15.1 Hz, 1H), 2.28 (m, 1H), 1.48 (s, 3H). $^{13}$C-NMR (500 MHz, CDCl$_3$): 172.35, 146.84, 146.14, 144.49, 144.24, 135.10, 132.53, 129.10, 127.68, 124.28, 120.44, 71.06, 43.01, 32.18, 25.08, 13.80. IR (cm$^{-1}$): 3419 (b), 2929 (w), 1658 (vs), 1596 (m), 1454 (w), 1238 (w), 1091 (w), 909 (m), 730 (w). HRMS (EI) calcd. for C$_{16}$H$_{14}$O$_3$: 254.0943. found: 254.0944.

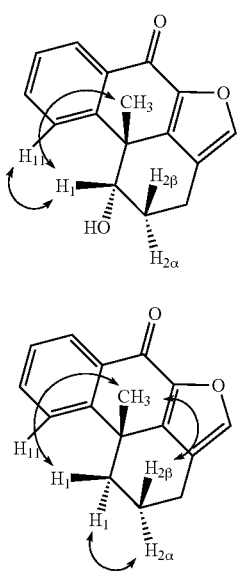

Identification of the stereochemistry was determined via careful $^1$H-NMR methods: NOESY1D (500 MHz, CDCl$_3$) of 19-Anti showed NOE signals between the methine CH (4.76 ppm, H$_1$) and the CH$_3$ (1.48 ppm, H$_{10a}$) and between the methine CH (4.76 ppm, H$_1$) and the aromatic CH (7.62 ppm, H$_{11}$). Additionally, the stereochemistry of 19-Syn was conclusively established by 2D-NMR (500 MHz, CDCl$_3$, COSY) showing NOE signals between the CH$_3$ (1.57 ppm, H$_{10a}$) and OH (1.95 ppm), the CH$_3$ (1.57 ppm, H$_{10a}$) and the CH (2.30 ppm, H$_{2\beta}$) and the methine CH (4.13 ppm, H$_1$) and the CH (2.19 ppm, H$_{2\alpha}$).

(1R,10bR)-2,3,6,10b-tetrahydro-10b-methyl-6-oxo-1H-phenanthro[10,1-bc]furan-1-yl acetate (19-Syn-Ac)

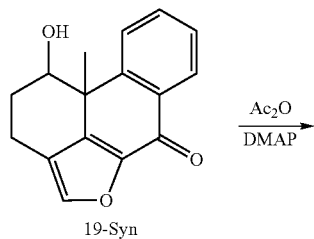

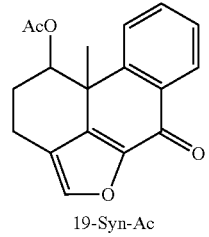

A solution of 10 mg (0.039 mmol, 1.0 eq) of alcohol 19-Syn in 0.50 mL of dry pyridine was stirred in a 5 mL flask at room temperature under argon. To this solution was sequentially added one crystal of N,N-dimethylaminopyridine (DMAP) and 50 μL (0.53 mmol, 13.0 eq) of Ac$_2$O. Stirring was continued at room temperature until the reaction was complete by TLC (1:1 hexane:EtOAc, R$_f$=0.51). Upon completion (~10 minutes), the solution was diluted with Et$_2$O and washed twice with 1.0 M HCl. The organic fraction was then washed sequentially with saturated NaHCO$_3$ and brine, dried over MgSO$_4$ and concentrated. Chromatography on silica gel (hexane/EtOAc) gave 5.6 mg (~50%) of acetate 19-Syn-Ac as a crystalline solid. The solid was then recrystallized from hexane/CH$_2$Cl$_2$ to give crystals suitable for X-ray defraction, R$_f$ 0.51 (1:1 hexane:EtOAc). Mp: 166.4-168.0° C. $^1$H-NMR (500 MHz, CDCl$_3$): 8.38 (1H, dd, J=7.8 Hz, J=1.7 Hz), 7.78 (1H, d, J=7.8 Hz), 7.52 (1H, m), 7.51 (1H, s), 7.46 (1H, dt, J=7.5 Hz, J=1.2 Hz), 5.14 (1H, dd, J=10.7 Hz, J=5.4 Hz), 2.96 (1H, m), 2.85 (1H, m), 2.35 (1H, m), 2.28 (3H, s), 2.24 (1H, m), 1.64 (3H, s). $^{13}$C-NMR (500 MHz, CDCl$_3$): 172.41, 170.19, 148.12, 145.07, 144.53, 143.80, 133.40, 132.41, 128.28, 127.56, 127.03, 120.75, 74.60, 40.07, 26.88, 25.21, 21.84, 16.77. IR (cm$^{-1}$): 3726 (w), 1740 (m), 1669 (s), 1597 (w), 1472 (w), 1457 (w), 1426 (w), 1237 (s), 1019 (w), 914 (w). HRMS (EI) calcd. for C$_{18}$H$_{16}$O$_4$: 296.1049. found: 296.1049. Structure confirmed by X-ray.

Data Collection for 19-Syn-Ac. A crystal (approximate dimensions 0.30×0.20×0.12 mm$^3$) was placed onto the tip of a 0.1 mm diameter glass capillary and mounted on a CCD area detector diffractometer for data collection at 173(2) K (SMART V5.054, Bruker Analytical X-ray Systems, Madison, Wis. (2001)). A preliminary set of cell constants was calculated from reflections harvested from three sets of 20 frames. These initial sets of frames were oriented such that orthogonal wedges of reciprocal space were surveyed. This produced initial orientation matrices determined from 34 reflections. The data collection was carried out using MoKα radiation (graphite monochromator) with a frame time of 30 seconds and a detector distance of 4.9 cm. A randomly oriented region of reciprocal space was surveyed to the extent of one sphere and to a resolution of 0.84 Å. Four major sections of frames were collected with 0.30° steps in ω at four different φ settings and a detector position of −28° in 2θ. The intensity data were corrected for absorption and decay (SADABS; Blessing (1995) supra). Final cell constants were calculated from 2502 strong reflections from the actual data collection after integration (SAINT; SAINT+V6.45, Bruker Analytical X-Ray Systems, Madison, Wis. (2003)).

Structure Solution and Refinement of 19-Syn-Ac. The structure was solved using Bruker SHELXTL (SHELXTL V6.14, Bruker Analytical X-Ray Systems, Madison, Wis. (2000)) and refined using Bruker SHELXTL (SHELXTL V6.14, Bruker Analytical X-Ray Systems, Madison, Wis. (2000)). The space group P2$_1$/c was determined based on systematic absences and intensity statistics. A direct-methods solution was calculated which provided most non-hydrogen atoms from the E-map. Full-matrix least squares/difference Fourier cycles were performed which located the remaining non-hydrogen atoms. All non-hydrogen atoms were refined with anisotropic displacement parameters. All hydrogen atoms were placed in ideal positions and refined as riding atoms with relative isotropic displacement parameters. The final full matrix least squares refinement converged to R1=0.0530 and wR2=0.1103 (F², all data).

Example 3

Synthesis of Viridin Furanosteroids

Using the same approach for synthesis of 19-syn, a family of viridin furanosteroids (1a-1d) can be produced.

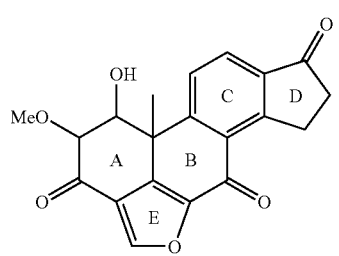
1a

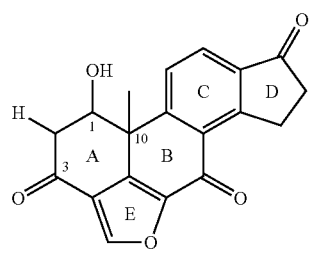
1b

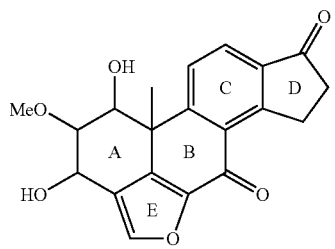
1c

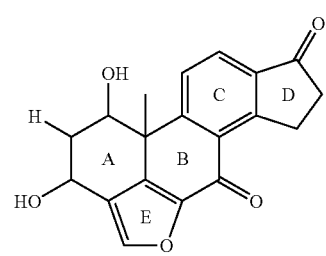
1d

For example, thermolysis of alkyne oxazole 22, produced from indanone derivative 21, followed by in situ silylation leads directly to phenol derivative 23, following the now well-established pathway of Diels-Alder/retro-Diels-Alder reaction/tautomerization (Scheme 5). Compound 23 is then employed to construct aldehydes of general structure 24 and subsequently furanosteroids 25. For X=O, 25 affords demethoxyviridin (26) upon hydrolysis. For X=β-OH hydrolysis affords demethoxyviridiol (27). As precedent for the transformation of 22 to 23, model system 11e gave a 50% overall yield of the furanoester 28 employing an analogous sequence.

Scheme 5

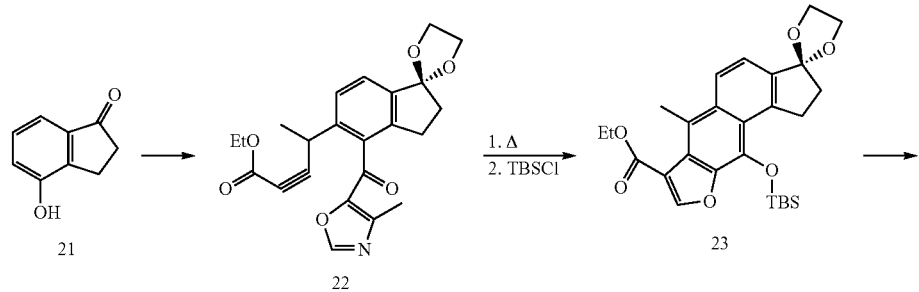

-continued
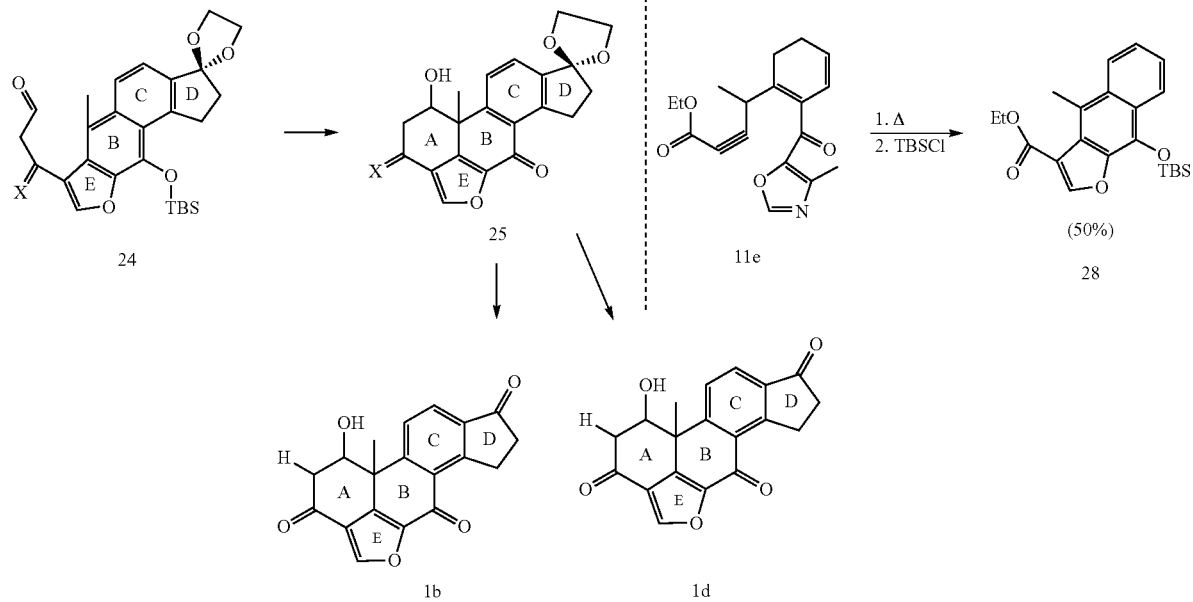
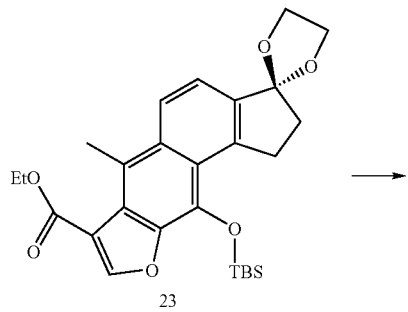
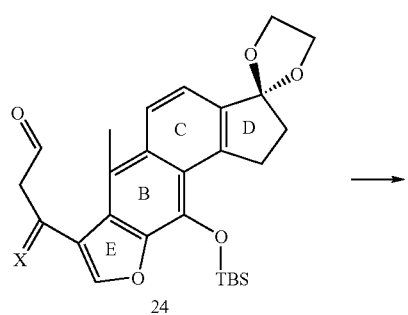

The synthesis of 22 begins with the commercially available (and easily prepared on 50 gram scales) indanone derivative 21 (Scheme 6; Kelly, et al. (1988) *J. Am. Chem. Soc.* 110: 6471). This material can be converted in three steps to the Boc derivative 31, involving ketalization (21→29), formylation (29→30), and anionic Fries rearrangement followed by trapping with Boc$_2$O (30→31). These steps are known in the art (Kelly, et al. (1988) supra) and efficient for the synthesis of the closely related species 33 beginning with 21 (~20 gram scales). Further, 33 is a potential precursor for 31 in its own right by suitable functional group manipulation.

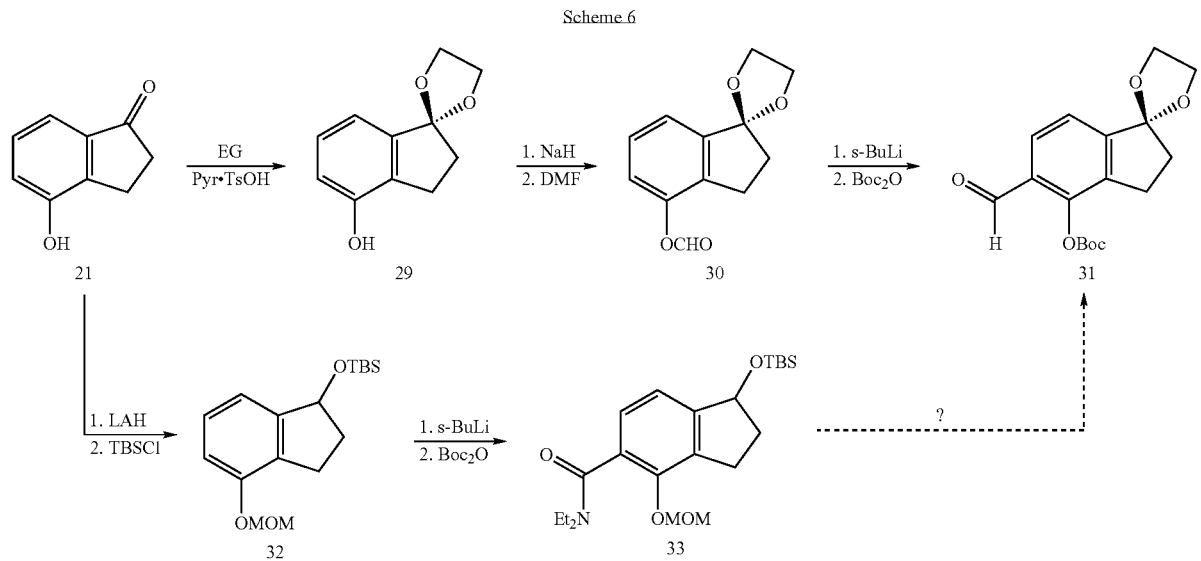

As with the synthesis of the viridin model, 31 is convertible to the triflate derivative 34 in essentially one step, employing the Pettus sequence followed by in situ trapping with Tf$_2$O (Scheme 7; Van De Water, et al. (2000) *J. Am. Chem. Soc.* 122(27):6502). Further elaboration of 32 to 22 is carried out utilizing the straightforward five-step sequence described for the preparation of 11e (see, Scheme 2). Thermolysis of 22 with in situ silylation affords the desired tetracyclic furan derivative 23. Each of these steps has been successfully demonstrated with closely related model compounds (vide supra).

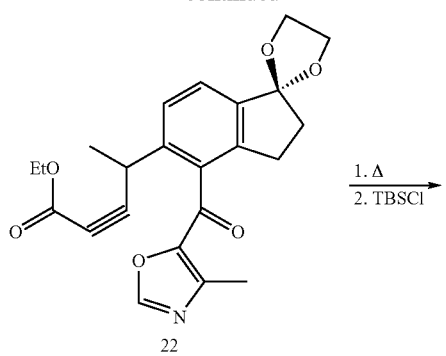

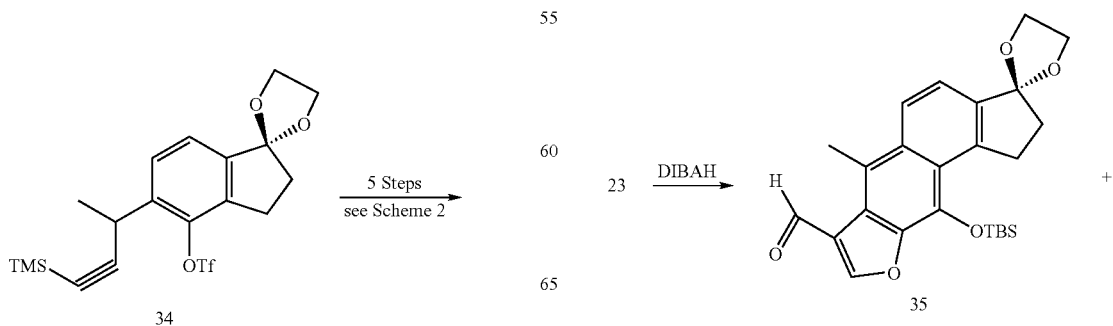

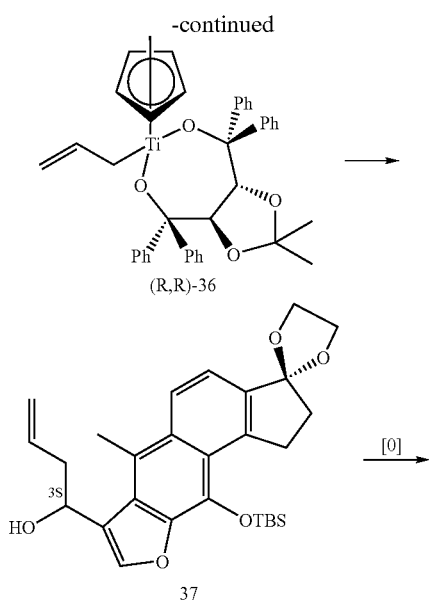

(R,R)-36

37

38

Along with a C1-hydroxyl group, the naturally occurring viridins have an oxygen functionality at C3 (X=O or β-hydroxy in III, Scheme 1). This substituent can be introduced beginning with DIBAH reduction of ester 23 to the corresponding aldehyde 35 (Scheme 7). Enantioselective allylation is then carried out employing the Hafner/Cossy reagent (R,R)-36 (Hafner, et al. (1992) *J. Am. Chem. Soc.* 114:2321; Bouz & Cossy (2003) *Org. Lett* 5:995; Delosseux, et al. (2003) *J. Org. Lett.* 5:4037), which exhibits nearly exclusive Si-face enantioselectivity in its reaction with aromatic aldehydes. The resulting S-configuration at C3 in 37 corresponds to that found in the naturally occurring viridins 1c and 1d. Oxidative cleavage with the reagent system $OsO_4/NMO/NaIO_4$ then affords the tethered aldehyde 38 under conditions in which the furan ring is known to be stable (Bouz & Cossy (2003) *Org. Lett.* 5:3029).

To achieve diastereoselectivity in closing ring A of the furanosteroid skeleton, a large hydroxyl protecting group P is introduced in 38 (Scheme 8). This substituent occupies a pseudo-equatorial position in conformation 38-eq leading to the desired aldol product 39, which may be sterically favored over the pseudo-axial conformation 38-ax. Minimization studies on 39 and 40 provide $\Delta\Delta H_{39:40}$ values approaching ~1 kcal as P varies from TMS to TBS to TBDPS, based upon equilibrium geometries and associated heat of formation calculated at the AM1 level using Spartan '02 v1.0.43 (Wavefunction Inc., Irvine, Calif.).

Scheme 8

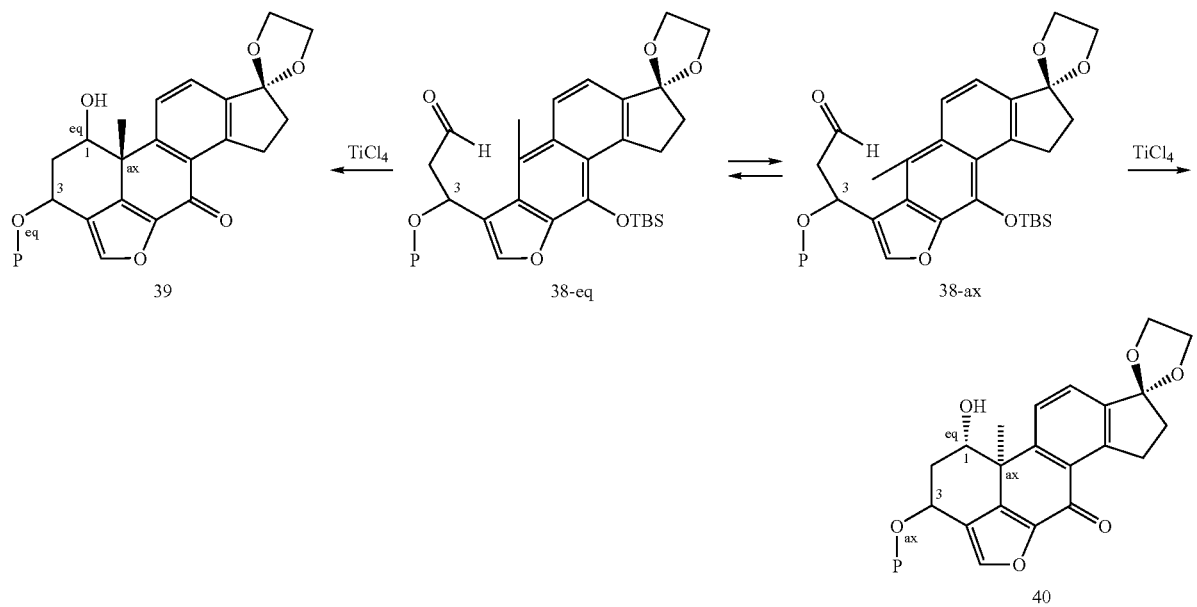

P = H, TBS, TBDPS, etc.

As an alternative, the approach set forth in Scheme 9 is employed. An interesting possibility arises when P=H or Bn in 39, where the reactive conformation is restricted as in 42 shown in Scheme 9 (chelation control; Reetz (1984) *Angew. Chem. Int. Ed. Engl.* 23:56-569; Reetz and Jung (1983) *J. Am. Chem. Soc.* 105:4833). In this case diastereoselectivity is governed solely by the stereochemistry of the C3-hydroxyl group, since the C1, C3 and C10-substituents are geometrically constrained to the same face of ring A. Consequently, aldol condensation of 41 produces exclusively the desired syn-relationship between C1 and C10 in 42, which on deprotection (for P=Bn) and mild acid hydrolysis (Sterzycki (1979) *Synthesis* 724) affords enantiomerically pure demethoxyviridiol (1d). Similar β-alkoxyaldehyde/Mukaiyama-type condensations employing TiCl$_4$ are known in the art (Reetz (1983) supra; Reetz (1984) supra). Also, oxidation of 42 (P=H) employing the Dess-Martin periodinane (Dess & Martin (1991) *J. Am. Chem. Soc.* 113:3850) followed by hydrolysis generates demethoxyviridin (1b) of natural absolute configuration. Finally, selective dehydration of the labile C3-hydroxyl group gives an allylic alcohol 43 directly related to an advanced intermediate in the Sorensen synthesis of viridin (1a) (OTBS replaces ketal in 43; Anderson, et al. (2004) supra).

Example 4

Synthesis of a Wortmannin Model

Ring A closure of a wortmannin (2) series was also conducted. The strained lactone ring in these compounds is known to be sensitive. The initial experiments were carried out with the alkyne oxazole 11e (R=Et), prepared in 75% yield by carboethoxylation of the parent alkyne 11b (Scheme 10; Vedejs & Piotrowski (1993) *J. Org. Chem.* 58(6):1341). Compound 11e gave a 50% yield of the TBS-protected phenol 44e on thermolysis in o-xylene followed by silylation. Subsequently, an intermolecular Mukaiyama-like aldol condensation with formaldehyde was conducted to set the stage for lactonization. The TiCl$_4$-catalyzed condensation of 44e with (CH$_2$O)$_n$ gave a >70% yield of the vinylogous aldol product 45e, which proved to be reasonably stable to retro-aldol cleavage. In spite of this stability, however, lactone ring closure was problematic with this substrate. As an alternative, t-butyl ester 45f (R=t-Bu), obtained in 65-70% yield upon brief heating of alkyne oxazole 11f in o-xylene followed by silylation, was employed. In contrast to ethyl ester 44e, 44f underwent concomitant hydrolysis and hydroxymethylation with (CH$_2$O)$_n$/TiCl$_4$, cleanly producing the corresponding

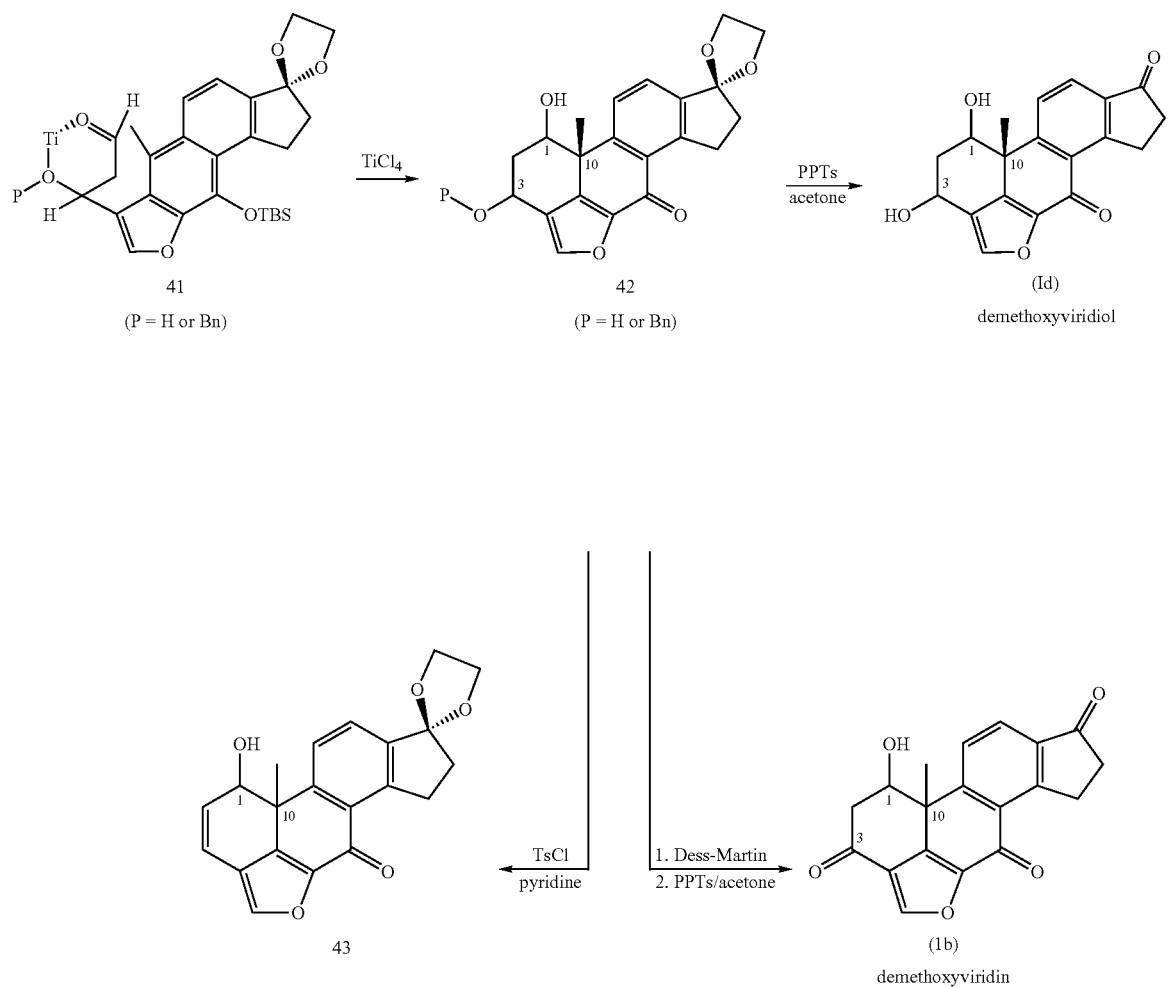

acid derivative 46. Treatment of crude 46 with POCl₃/pyridine gave a ~25-50% overall yield of the desired wortmannin model substrate 47.

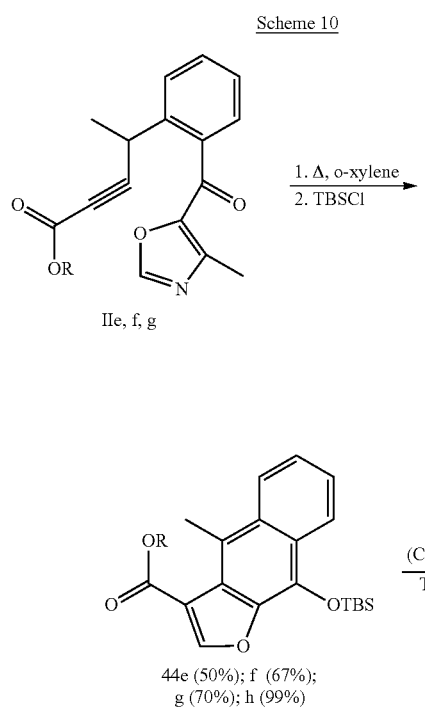

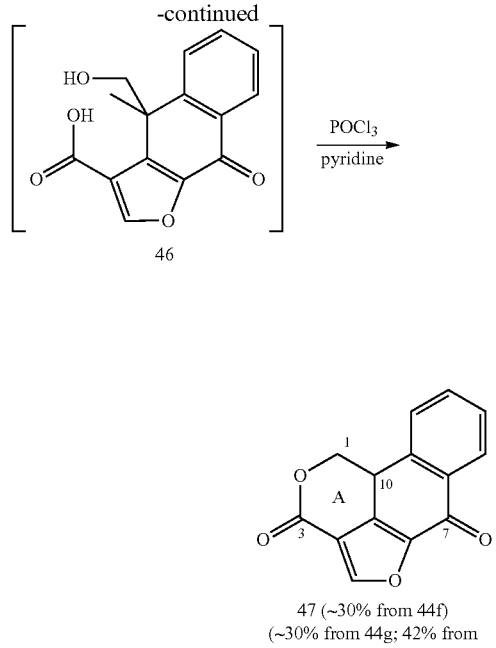

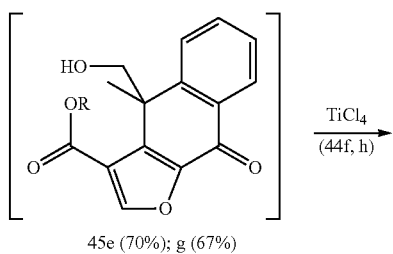

Example 5

Synthesis of Wortmannin Furanosteroids

Synthesis of 1'-Desacetoxywortmannin (2b). The prior art indicates that a highly stereoselective reduction of enantiomerically pure ketal 48 to the corresponding trans-fused enolate derivative 49 (Scheme 11) can be achieved (Zhou & Wei (1990) *Synthesis* 822).

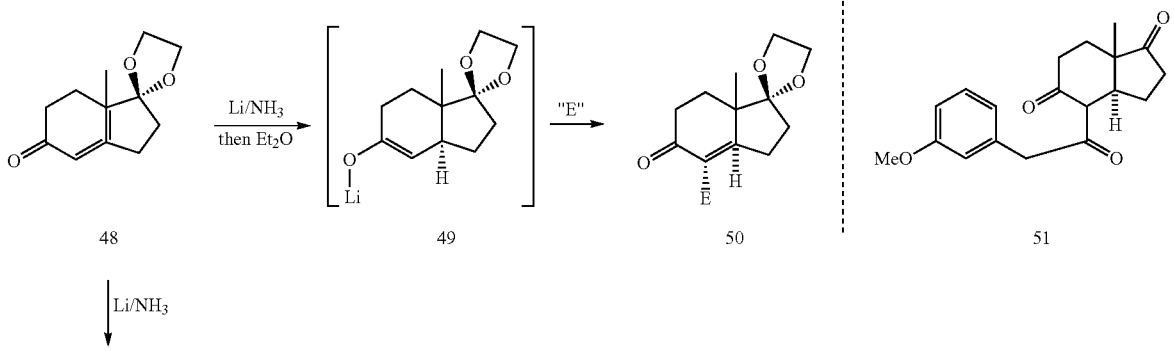

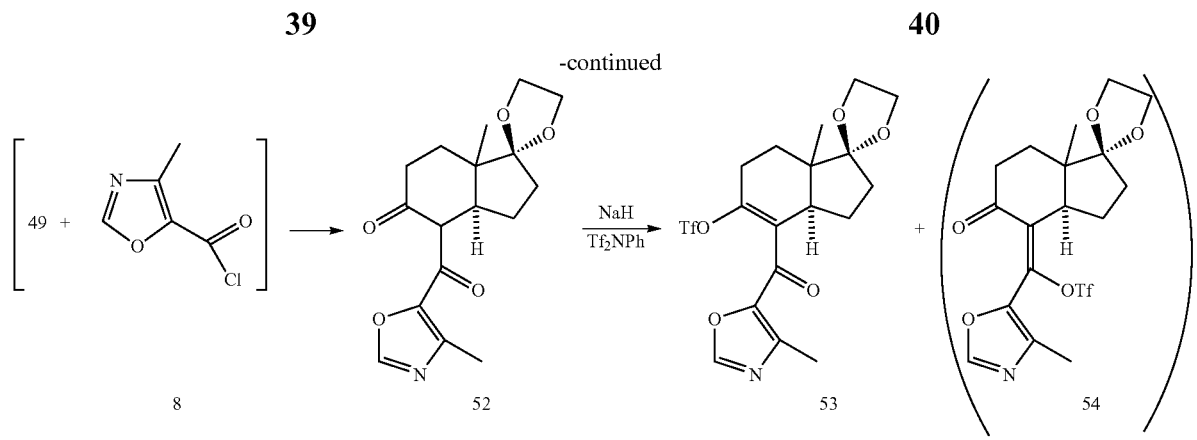

In situ trapping of 49 with Michael acceptors "E" then gives high yields of adducts 50. Similarly, an efficient synthesis of the estrone precursor 51 has been achieved by reductive acylation of the parent indenedione (again with excellent trans-selectivity; Kiegiel (1988) *J. Org. Chem.* 53:5535). Analogously, the keto-oxazole derivative 52 is synthesized by condensation of 49 with the oxazole acid chloride 8 (Sindler-Kulyk, et al. (1994) *Heterocycles* 38:791; Boulos & Schulman (1998) *Heterocyclic Chem.* 35:859). Next, triflation of 52 with NaH/Tf$_2$NPh affords the endo-enol triflate 53 in highly regioselective fashion, since the alternative exo-enol triflate 54 has significant allylic strain.

Model studies provide support for these steps (Scheme 12). Acylation of cyclohexanone 55 with the oxazole acid chloride 8 gave a 54% yield of the di-keto derivative 56, together with <5% of the corresponding O-acylated material iso-56. Subsequent triflation of 56 with PhNTf$_2$/NaH then afforded 67% of the desired internal triflate 57-endo together with ~3% of the exo-regioisomer 57-exo (>20:1; Hamaoka, et al. (1994) *Heterocycles* 37:167; Comins & Dehghani (1992) *Tetrahedron Lett.* 33:6299; Stang, et al. (1982) *Synthesis* 85). The two triflates were differentiated by reduction with DIBAH to the corresponding alcohols 58 and 59, which had the expected NMR signals for the newly introduced methine alcohol protons (singlet for the bold H in 58; doublet of doublets for the corresponding H in 59).

Scheme 12

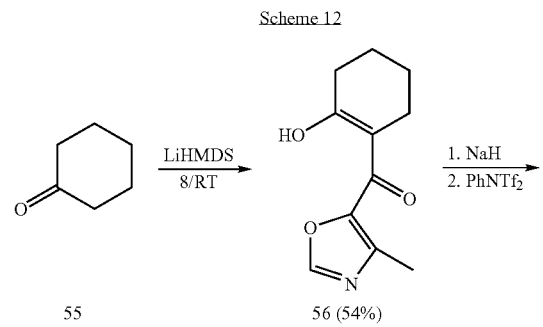

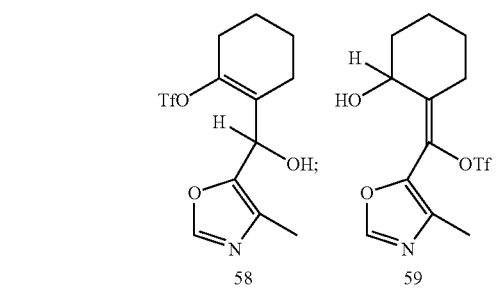

The conversion of triflate 53 to the oxazole ester 62 and subsequently to furanoacid 64 is depicted in Scheme 13. Benzyl ester 62 is generated by coupling triflate 53 with the butynylcuprate derivative 60, prepared from 1-trimethylsilyl-butyne by lithiation (n-BuLi) and transmetallation with CuI (Scheme 13; Lam & Pattenden (2002) *Angew. Chem. Int. Ed.* 41:508). Conversion of 61 to the benzyl ester 62 is carried out employing the same two-step procedure used to prepare model compound 11g (see Scheme 10); desilylation and carboxylation with the reagent system Pd/CO/O$_2$/BnOH/DMF (Izawa, et al. (2004) *Bull. Chem. Soc. Jpn.* 77:2033-2045). Finally, thermolysis of 62 to 63, with in situ silylation, affords the furanoester 63, which on hydrogenolysis gives the acid 64.

Scheme 13

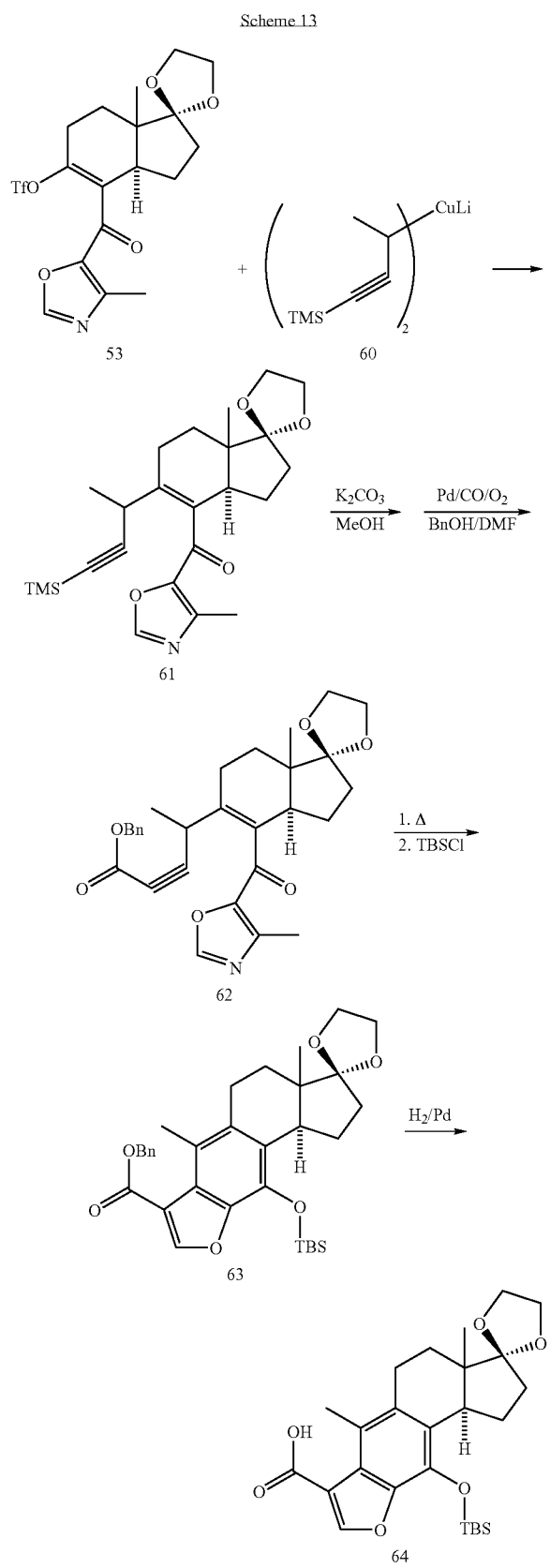

Regarding the coupling of 53 and 60, the utility of propargyl cuprates related to 60 has been demonstrated, wherein the bulky TMS group effectively eliminates reaction through the corresponding allenyl cuprate tautomer (Ganem (1974) *Tetrahedron Lett.* 4467; Commercon, et al. (1975) *J. Organomet. Chem.* 93:415; Lam & Pattenden (2002) supra; Corey & Kirst (1968) *Tetrahedron Lett.* 5041; Corey & Rucker (1982) *Tetrahedron Lett.* 23:719). For example, near quantitative conversion of triflate 65 to the highly functionalized alkyne 67 on coupling with the cuprate derivative 66 has been achieved (Scheme 14; Lam & Pattenden (2002) supra). The reactivity of the 2°-alkynylcuprate 60 is expected to be comparable, since this derivative has minimal steric hindrance. Alternatively, the initial coupling of 53 can be effected with the Pattenden reagent 66 and methylation delayed until after phenol formation.

Scheme 14

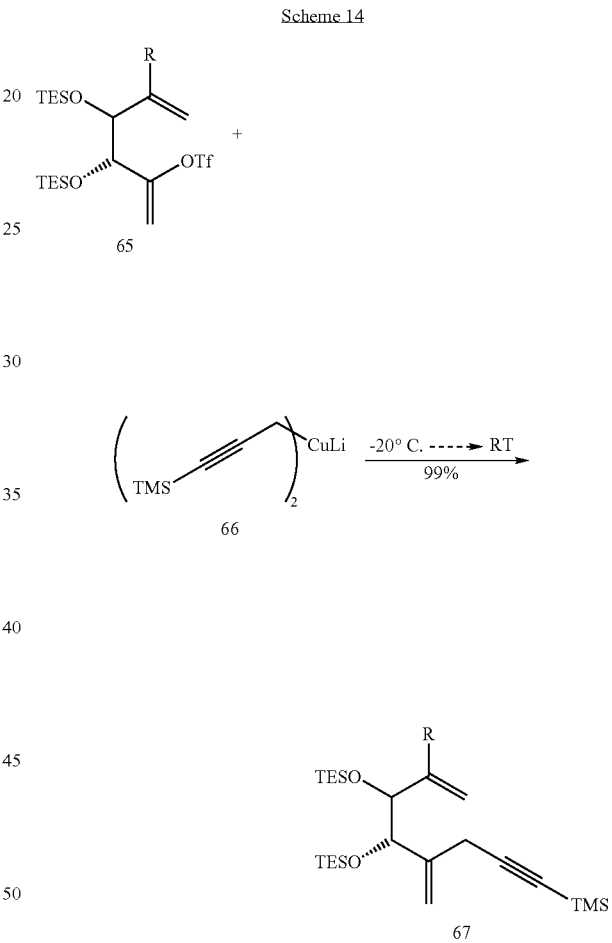

Introduction of the furanolactone ring into 2b is shown in Scheme 15. Based on the prior art (Freiermuth, et al. (2001) *Helv. Chim. Acta* 84:3796; Garduno-Ramirez, et al. (2001) *J. Nat. Prod.* 64:432; Torres, et al. (1989) *Phytochemistry* 28:3093; Burgueno-Tapia, et al. (2001) *J. Nat. Prod.* 64:518) and the results presented in Scheme 10, "de-aromatization" of such phenols does not present a significant thermodynamic barrier. Rather, these reactions are better viewed as vinylogous Mukaiyama aldol condensations driven by relief of strong peri-interactions (Burgueno-Tapia, et al. (2001) supra). Some indication of the stability of such intermediates is given by the fact that degradation of 2b to 69 requires 1 hour boiling in 2N HCl (Haefliger & Hauser (1973) *Helv. Chim. Acta.* 56:2901).

Scheme 15

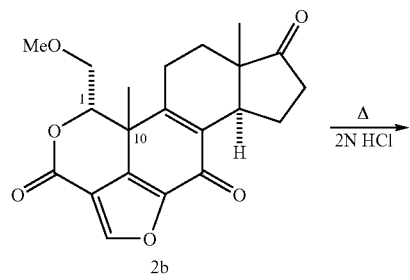

Scheme 16

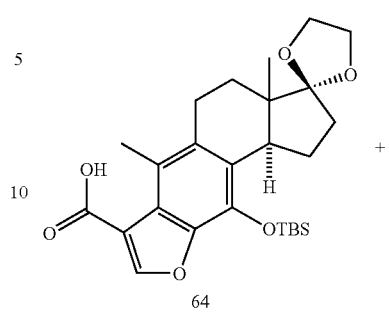

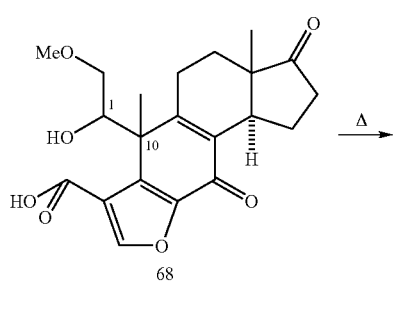

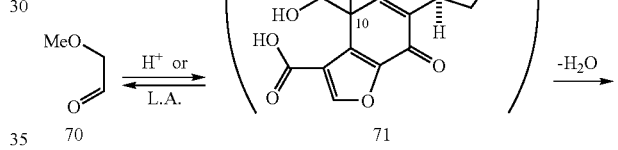

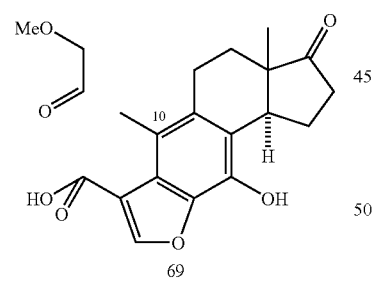

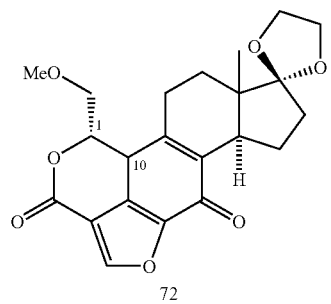

Acid catalyzed condensation of furanoacid 64 and methoxyacetaldehyde (70), essentially the reverse of the degradation of 2b, is depicted in Scheme 16. It is expected that equilibrium concentrations of aldol products 71 will be established, ultimately rendered irreversible by lactonization to afford 72. It is contemplated that the structural rigidity of 64 will facilitate stereochemical control of the condensation of 64 and 70. As with most steroidal compounds wortmannin (2a) and 11-desacetoxywortmannin (2b) have well defined faces, with the α-face having distinctly less steric crowding (particularly factoring out the C1-methoxymethyl group). This is a consequence of the axial methyl groups at C10 and C13, as can be seen in the X-ray crystal structure of 2a.

Models and MM2 minimizations indicate that the same facial bias exists in furanoacid 64, where the C13 methyl group shields the β-face of C10 to approach by electrophiles. Therefore, the desired α-isomer 71a should be favored under kinetic control and afford the wortmannin ketal 72α (Scheme 17). It is also contemplated that 72α will predominate under thermodynamic control, since this orientation accommodates the large methoxymethyl group in a pseudoequatorial position, far removed from the axial C13-methyl.

Scheme 17

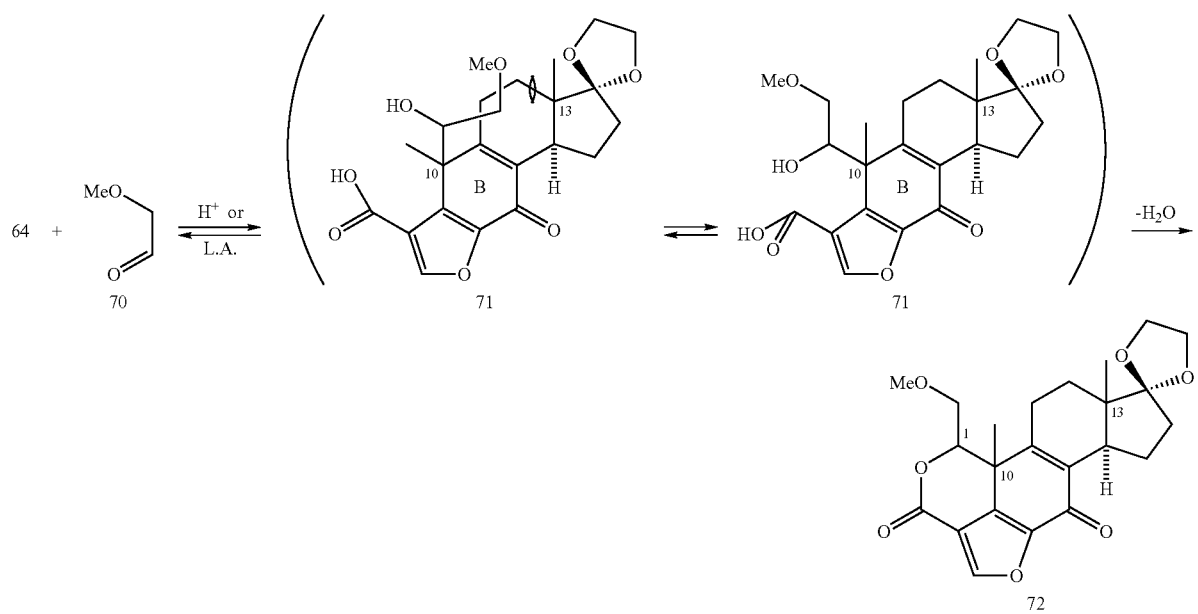

The X-ray data for 2a indicates that the "natural" α-stereochemistry at C1 is thermodynamically favored, even though this configuration requires an axial orientation of the methoxymethyl group. However, steric crowding in this case is minimal since there are no other α-face substituents on rings A, B and E. In contrast, models show that the "unnatural" β-configuration suffers from a strong transannular interaction with the methylene hydrogens at C11, in essence corresponding to a "1,4-flagpole" interaction in boat cyclohexane. The "unnatural" β-configuration at C1 also is destabilized by a strong gauche interaction with the C10-methyl group. The same circumstances are found in 11-desacetoxywortmannin (2b) for epimers 1R-2b and 1S-2b. In stereo drawings and MM2 derived structures, the "1,4-flagpole" interaction is present in 1R-2b and absent in 1S-2b. Partly due to this interaction, as well as torsional strain, the axial α-configuration at C1 is calculated to be significantly more stable, with a 3.6 kcal difference in heat of formation between 1R-2b and 1S-2b at the AM1 level of computation. It follows that if each step in converting 64 to 11-desacetoxywortmannin (2b) is carried out under equilibrium control the natural isomer will predominate. As disclosed herein, the synthesis of 2b requires 8-9 steps from readily available indenedione 48, a significant improvement over the prior art (Sato, et al. (1996) supra; Mizutani, et al. (2002) supra).

Scheme 18 depicts an alternative means of inserting methoxyacetaldehyde, where the $C_1$-$C_{10}$ bond results from intramolecular capture of carbocation 75. While various means are available for generating 75, the thiolacetoxy derivative 74 is a particularly useful precursor because of its stability and ease of preparation. This material is derived by base-catalyzed alkylation of the furanoacid 64 with α-chlorosulfide 73, itself prepared by chlorination of commercially available [(2-methoxyethyl)thio]-benzene (76) (Scheme 19; R=$CH_2OMe$) (Groth, et al. (1994) Liebigs Ann. Chem. 665; Iqbal & Shukla (1991) A. Tetrahedron 47:8753; Benneche, et al. (1989) Acta Chemica Scandinavica 43:74; Avolio, et al. (1999) Synlett. 11:1820). Many such transformations are known in the art and this methodology is compatible with a wide range of functionality. Moreover, it has been shown that thiolacetoxy compounds of general structure 78 are excellent sources for carbocations 79, producing with $SO_2Cl_2$/$CH_2Cl_2$ the highly reactive chloroacetoxy derivatives 80 (Groth, et al. (1994) supra). Thus, while 74 is expected to be stable and easily handled, $SO_2Cl_2$-induced ionization provides a ready source of cation 75, which should cyclize in diastereoselective fashion to afford 11-desacetoxywortmannin ketal (2b-ketal). Although cation 75 formally corresponds to the less favorable Z-conformation of an ester, the vacant p-orbital should mitigate the stereoelectronic effect normally associated with stabilizing the E-configuration (i.e., the oxygen p-π* interaction is less important than lone pair conjugation with the adjacent carbocation p-orbital). An alternative and very mild means of ionizing 74 would employ $HgCl_2$/$CH_2Cl_2$ (Kishi (1979) J. Nat. Prod. 42:549).

Scheme 18

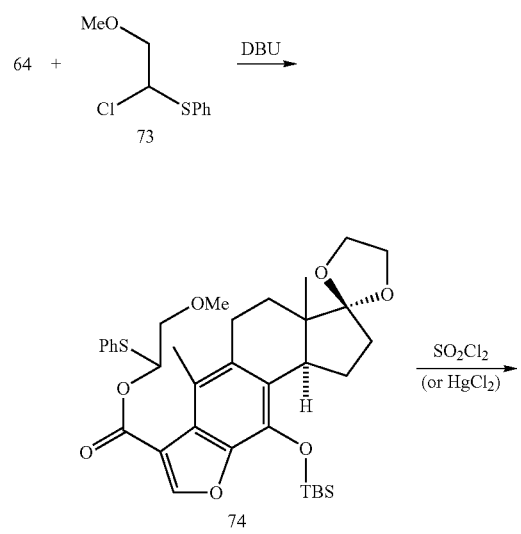

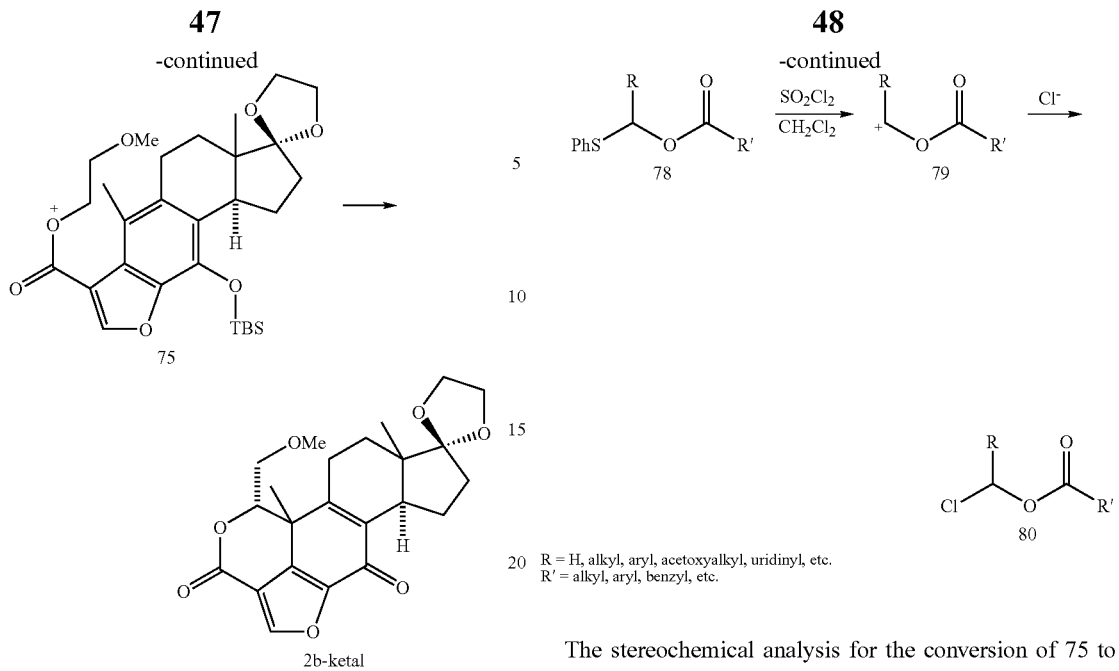

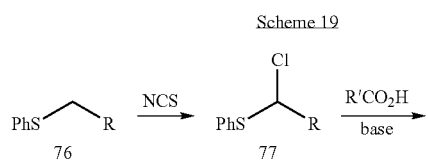

The stereochemical analysis for the conversion of 75 to 2b-ketal is similar to that presented in Scheme 17 for the intermolecular pathway. Cation 75 is generated from 74 as described in Scheme 18 and allowed to undergo nucleophilic capture at C10 (Reaction at C21 is unlikely since this would introduce significant ring strain and also place a positive charge adjacent to the ester carbonyl group). Four conformations of 75 are geometrically positioned to participate in bond formation between C1 and C10 (Scheme 20).

R = H, alkyl, aryl, acetoxyalkyl, uridinyl, etc.
R' = alkyl, aryl, benzyl, etc.

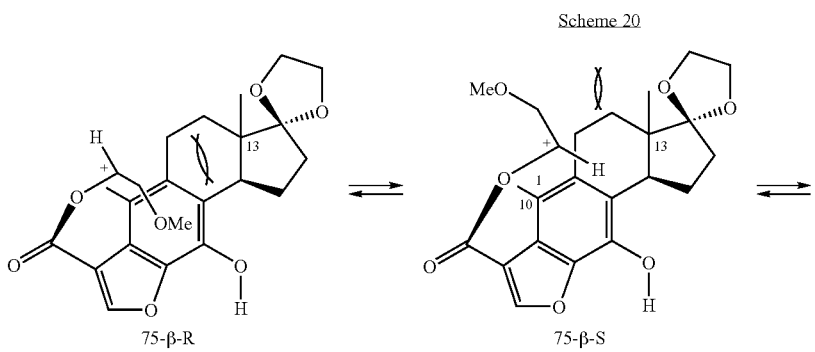

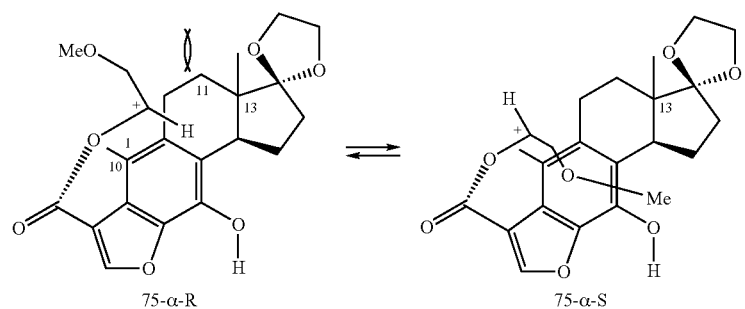

However, the β-conformations 75-β-R and 75-β-S encounter steric crowding with the C-13 methyl group and are less favorable (α and β refer to the face of the molecule; R and S denote the absolute stereochemistry of the newly formed chiral center at C1). Of the remaining α-conformations, 75-α-S affords the natural stereochemistry of 11-desacetoxywortmannin ketal (2b-ketal), while 75-α-R produces the C-1 epimer. Comparing these two, 75-α-S appears to have fewer non-bonded interactions than 75-α-R and is expected to predominate at equilibrium. While 75-α-S has the larger methoxymethyl group residing under the framework of the furanosteroid skeleton, this orientation produces little steric crowding since all proximal ring atoms are sp²-hybridized. In contrast, conformer 75-α-R has a nascent eclipsing interaction between the C1-methoxymethyl group and the C11 methylene hydrogens. Ultimately this conformation gives rise to the "boat-flagpole" interaction and torsional strain found in 1R-2b, which calculations show to be ~3.6 kcal less stable than 1S-2b. Therefore, to the extent that product stability is reflected in the transition state leading to 1b-α-R, the desired S-configuration at C1 would be highly favored. Mild acid hydrolysis then affords 11-desacetoxywortmannin (2b) in enantiomerically pure form.

Synthesis of Wortmannin (2a). Wortmannin (2a) differs from 11-desacetoxywortmannin (2b) only in having an 11-α-acetoxy substituent, and 2a can be synthesized following a route similar to that for 11-desacetoxywortmannin (2b). Alternatively, regio- and stereoselective oxidation of 2b to 2a can be employed, an approach that has a number of advantages (Scheme 21). Not the least of these is that the 11-α-acetoxy substituent would be introduced at the last stage of the synthesis, eliminating the need for multiple protecting groups. Because 2b is unusual in the fact that it has relatively few labile C—H bonds for such a highly oxygenated material, oxidation experiments are carried out on the C-17 ketal derivative 2b-ketal, leaving C11 as the only site activated by conjugation to a carbonyl group. A number of reagents can be employed to effect this oxidation, and Pb(OAc)₄ would produce 2a-ketal directly.

Scheme 21

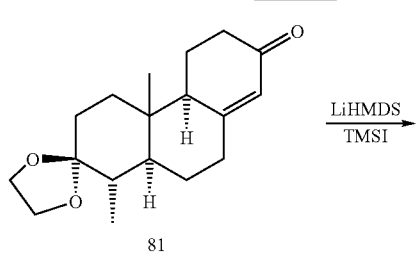

2b-ketal

Pb(OAc)₄
?

2a-ketal

Alternatively, studies on the closely related enone 81 are analogous to the desired conversion (Scheme 22) (Suryawanshi & Fuchs (1981) *Tetrahedron Lett.* 22:4201). In a stereo- and regioselective oxidation, the oxidation of 81 to 83 was effected with essentially 100% facial selectivity, via the intermediacy of the silyl dienol ether 82. Treatment of 82 with the very mild oxidant OXONE® afforded alcohol 83 in 92% overall yield.

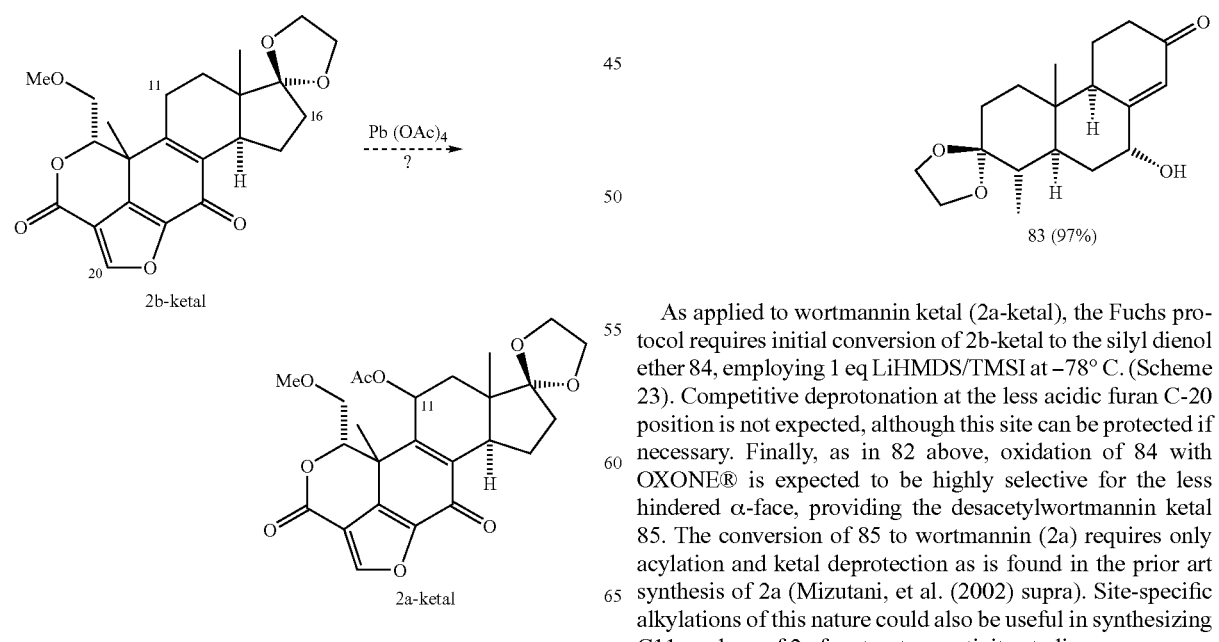

As applied to wortmannin ketal (2a-ketal), the Fuchs protocol requires initial conversion of 2b-ketal to the silyl dienol ether 84, employing 1 eq LiHMDS/TMSI at −78° C. (Scheme 23). Competitive deprotonation at the less acidic furan C-20 position is not expected, although this site can be protected if necessary. Finally, as in 82 above, oxidation of 84 with OXONE® is expected to be highly selective for the less hindered α-face, providing the desacetylwortmannin ketal 85. The conversion of 85 to wortmannin (2a) requires only acylation and ketal deprotection as is found in the prior art synthesis of 2a (Mizutani, et al. (2002) supra). Site-specific alkylations of this nature could also be useful in synthesizing C11-analogs of 2a for structure-activity studies.

Scheme 23

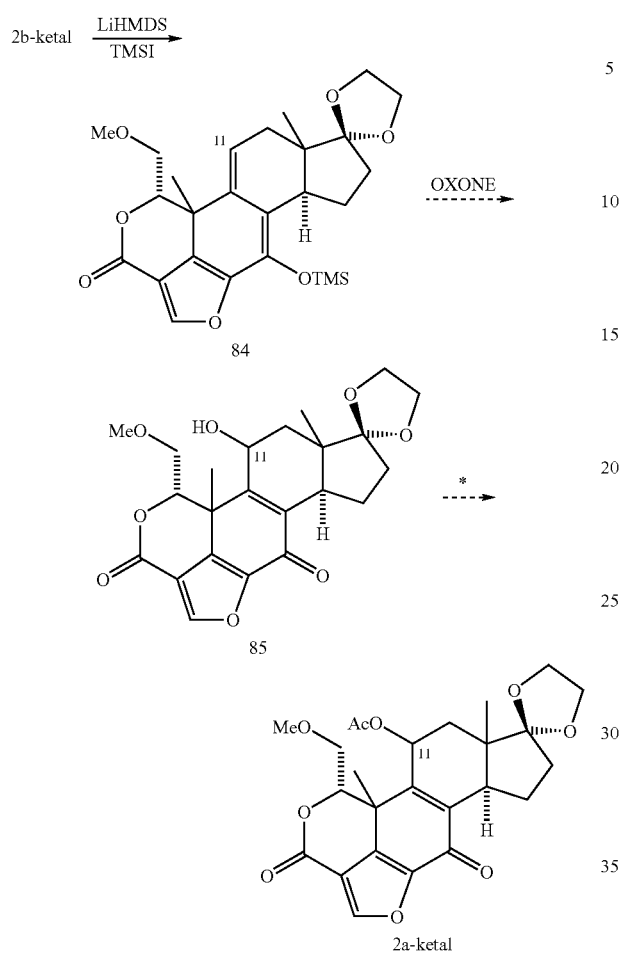

*Mizutani, et al. (2002) supra*

Example 6

Analogs of Viridian and Wortmannin Core Structures

To analyze the oxidation state and substitution pattern at the positions thought to be most crucial to PI3K inhibition (C3, C7 and C10), over twenty analogs containing the core structures of viridin and wortmannin were synthesized. Compounds 86-93 will be useful in comparing the effect of increasing oxidation level at C3 while maintaining the phenol oxidation state at C7 (86-89), as well as the same effect on ketone derivatives 90-93 having the wortmannin/viridin oxidation state at C7.

86

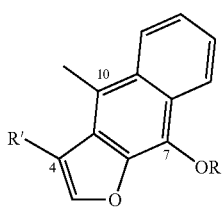

87

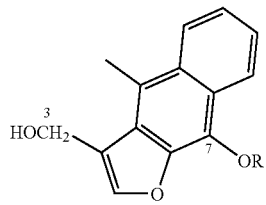

88

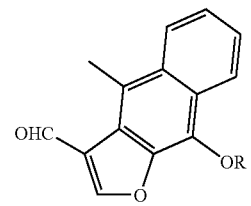

89

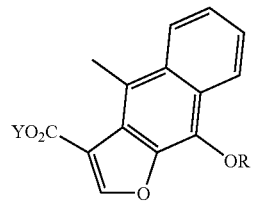

90

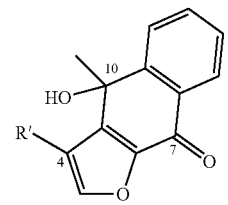

91

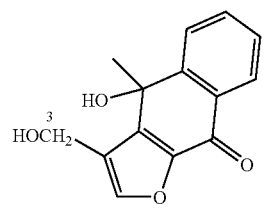

92

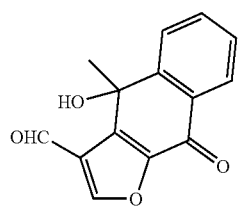

93

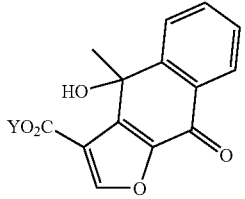

Similarly, compounds 94-99 will serve to evaluate the effect of variable oxidation level in the vinylogous substrates.

94 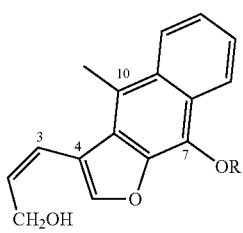
95 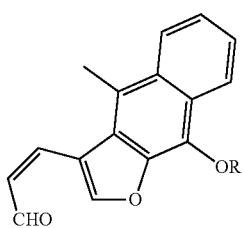
96 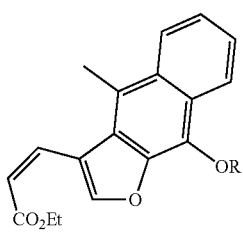
97 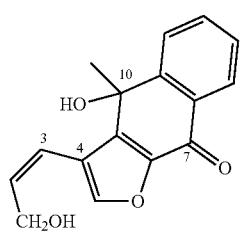
98 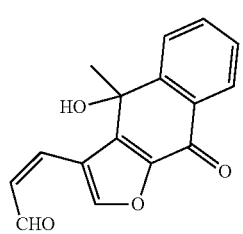
99 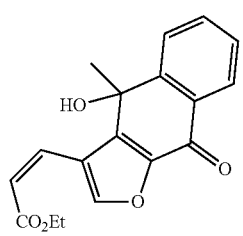
100 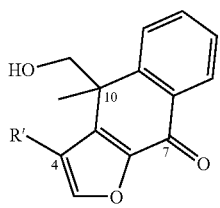
101 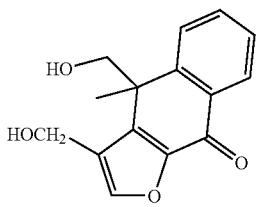
102 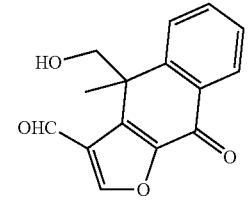
103 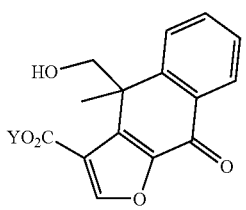
19S 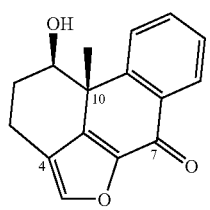
47 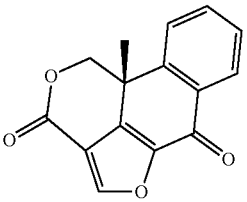
104 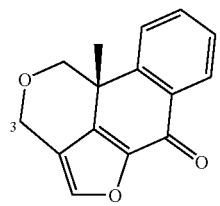
Furthermore, in addition to hydroxymethyl derivatives 100-103, Compounds 100-106 include the viridin and wortmannin analogs 19S and 47 and the novel substrates 104-106.

-continued

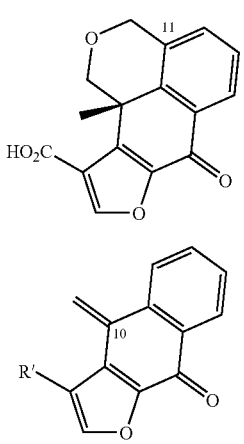

105

106

Wortmannin analog 47 possesses sub-micromolar activity against PI3K-Beta, and represents a promising drug scaffold to study substituent effects at C-1. Processes of the type depicted in Schemes 16 and 17 for introducing C-1 substituents in a stereoselective fashion have been demonstrated. For example, a solution of furanoacid 107 in CH$_2$Cl$_2$ was treated sequentially with (COCl)$_2$ (107→108), followed by in situ aldol condensation employing a slight excess of ethyl glyoxylate/TiCl$_4$ (Scheme 24). On stirring at room temperature and analysis by TLC, the very clean formation of lactone 111α was observed, which was isolated in 60% yield as a colorless crystalline solid. Within the limits of NMR and TLC detection, there was no evidence for formation of the corresponding epimeric lactone 111β.

The level of efficiency in the transformation of 107 to 111α is noteworthy, introducing in a single step what are arguably the most challenging structural features found in Wortmannin (a bisallylic quarternary carbon center and a highly reactive furanocyclohexadienone lactone unit). The mechanistic rationale for this efficiency involves rapid aldol-retro-aldol equilibration of initial adducts 109 and 110 followed by diastereoselective lactonization to give the more thermodynamically stable lactone 111α. Additional analogs can be synthesized employing the same methodology, and screened for attractive leads.

What is claimed is:

1. A method for synthesizing a furanosteroid comprising
   (a) subjecting a functionalized alkyne oxazole to thermolysis to produce a furo[2,3-b]phenol of structure II

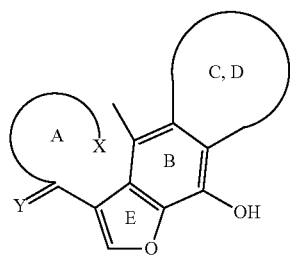

II

Scheme 24

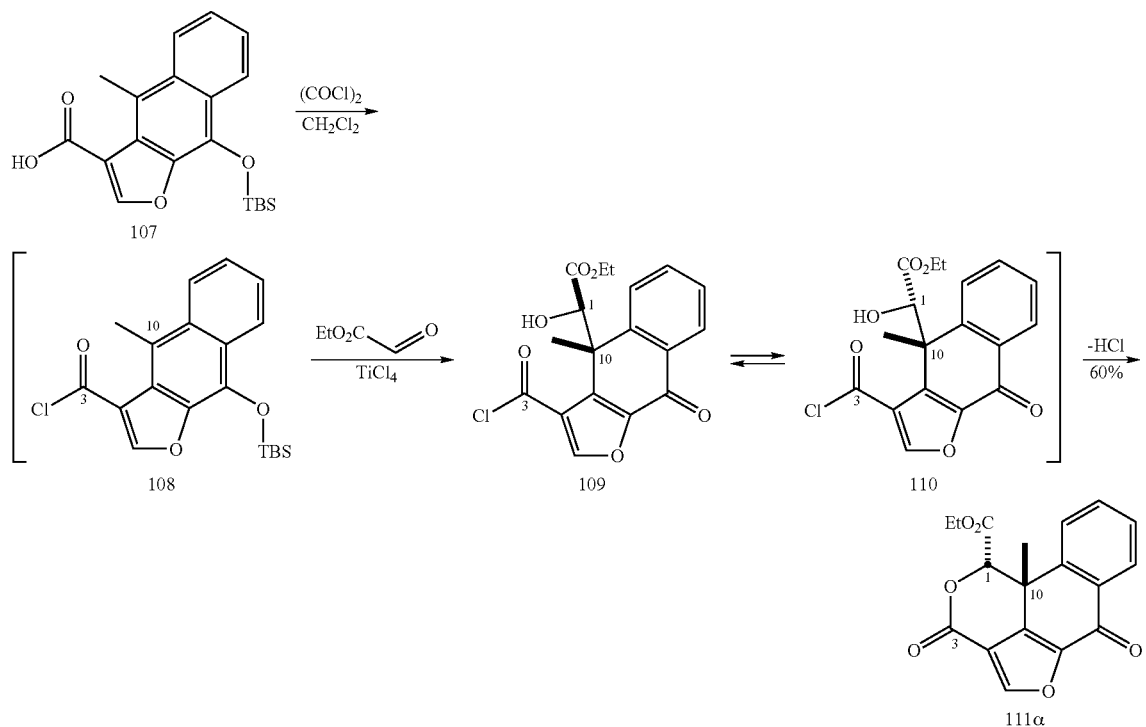

wherein
Y is H2, OH or O;
X is C=C, C=O, or a leaving group; and
(b) subjecting the furo[2,3-b]phenol to
(i) an intramolecular condensation reaction in the presence of a Lewis acid, or
(ii) an intermolecular condensation reaction with O=CH—R' wherein R' is alkyl or aryl, thereby synthesizing a furanosteroid.

* * * * *